(12) United States Patent
Hirata et al.

(10) Patent No.: US 8,396,546 B2
(45) Date of Patent: Mar. 12, 2013

(54) MACHINE CONTROL DEVICE, MACHINE SYSTEM, MACHINE CONTROL METHOD, AND RECORDING MEDIUM STORING MACHINE CONTROL PROGRAM

(75) Inventors: Masayuki Hirata, Suita (JP); Takufumi Yanagisawa, Suita (JP); Yukiyasu Kamitani, Soraku-Gun (JP); Hiroshi Yokoi, Bunkyo-Ku (JP); Toshiki Yoshimine, Suita (JP); Tetsu Goto, Suita (JP); Ryohei Fukuma, Soraku-Gun (JP); Ryu Kato, Bunkyo-Ku (JP)

(73) Assignees: Osaka University, Suita (JP); Advanced Telecommunications Research Institute International, Soraku-Gun (JP); The University of Tokyo, Tokyo (JP)

( * ) Notice: Subject to any disclaimer, the term of this patent is extended or adjusted under 35 U.S.C. 154(b) by 339 days.

(21) Appl. No.: 12/799,840

(22) Filed: May 3, 2010

(65) Prior Publication Data
US 2011/0218453 A1    Sep. 8, 2011

(30) Foreign Application Priority Data
Mar. 5, 2010 (JP) .................................. 2010-049814

(51) Int. Cl.
*A61B 5/04* (2006.01)
(52) U.S. Cl. ...................................................... 600/545
(58) Field of Classification Search .................. 600/544, 600/545
See application file for complete search history.

(56) References Cited

U.S. PATENT DOCUMENTS
6,731,964 B2 * 5/2004 Shenoy et al. ................ 600/372
7,120,486 B2   10/2006 Leuthardt et al.
(Continued)

OTHER PUBLICATIONS

F. Nijboer, et al., 2008, "A P300-based brain-computer interface for people with amyotrophic lateral sclerosis", Clin.Neurophysiol, 119, p. 1909-1916.

(Continued)

*Primary Examiner* — Navin Natnithithadha
*Assistant Examiner* — Etsub Berhanu
(74) *Attorney, Agent, or Firm* — Edwards Wildman Palmer LLP; David G. Conlin; David A. Tucker

(57) ABSTRACT

A machine control device includes: first decoders for estimating, from brain signal information, which one of body movements a user performs or images, based on learning using pairs of movements performed by the user and brain signal information, the body movements going toward one of first to nth body postures; second decoders for estimating from the brain signal information, an correct rate on the body movement estimation, based on learning using pairs of correct rates of the estimation of body movements and the brain signal information; and electric prosthetic arm control section for controlling an electric prosthetic arm to change stepwise its posture between first to nth postures via at least one intermediate posture therebetween, the first to nth postures corresponding to the first to nth body postures. The first decoders perform the estimation only when the estimated correct rate exceeds a threshold. When the first decoders estimate that the body movements goes toward a body posture different from the current one, the electric prosthetic arm control section changes the posture of the machine by performing a part of substeps of change from one of the first to nth body postures toward the posture associated with the body posture toward which the estimated body movement goes. This configuration allows a user to control a brain-signal-based machine to perform a natural movement without a long-term training and much brain information.

10 Claims, 11 Drawing Sheets

U.S. PATENT DOCUMENTS

| | | | | |
|---|---|---|---|---|
| 7,209,788 | B2* | 4/2007 | Nicolelis et al. | 607/48 |
| 7,873,411 | B2* | 1/2011 | Eda et al. | 600/544 |
| 2002/0103429 | A1* | 8/2002 | deCharms | 600/410 |
| 2006/0167371 | A1* | 7/2006 | Flaherty et al. | 600/545 |
| 2007/0032738 | A1* | 2/2007 | Flaherty et al. | 600/545 |
| 2008/0280774 | A1* | 11/2008 | Burczynski et al. | 435/6 |
| 2009/0124886 | A1* | 5/2009 | Wang et al. | 600/410 |

OTHER PUBLICATIONS

E.C. Leuthardt, et al., 2006. "The emerging world of motor neuroprosthetics: a neurosurgical perspective", Neurosurgery, 59, p. 1-14.

L.R. Hochberg, et al., 2006. "Neuronal ensemble control of prosthetic devices by a human with tetraplegia", Nature, 442, p. 164-171.

M. Velliste, et al., 2008. "Cortical control of a prosthetic arm for self-feeding", Nature, 453, p. 1098-1101.

G. Schalk et al., 2008, "Two-dimensional movement control using electrocorticographic signals in humans", J Neural Eng, 5(1): 75-84, p. 1-21.

Kamitani, Y. and F. Tong, "Decoding the visual and subjective contents of the human brain". Nat Neurosci. 8(5): p. 679-685, 2005.

* cited by examiner

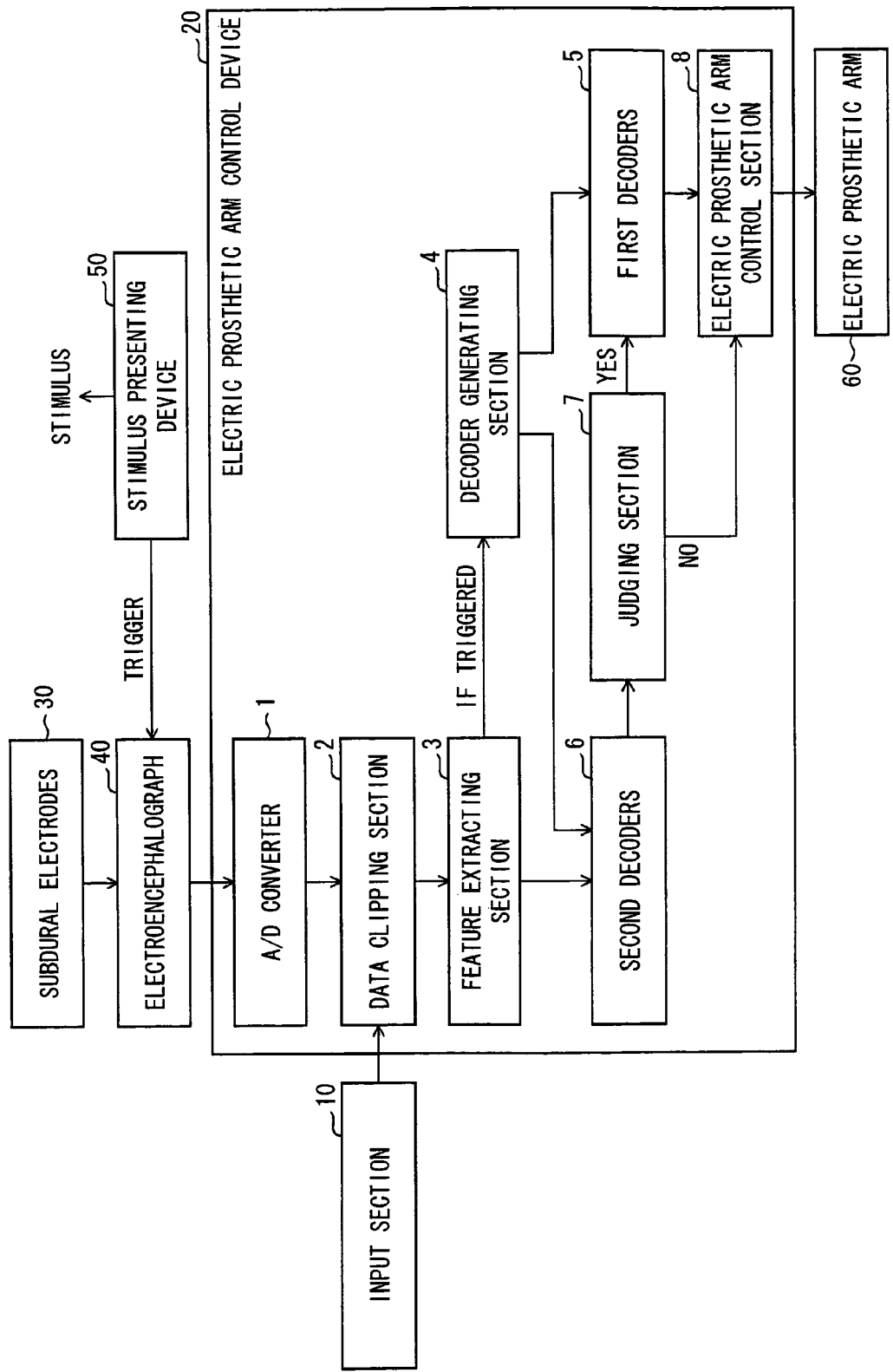
F I G. 1

F I G. 3
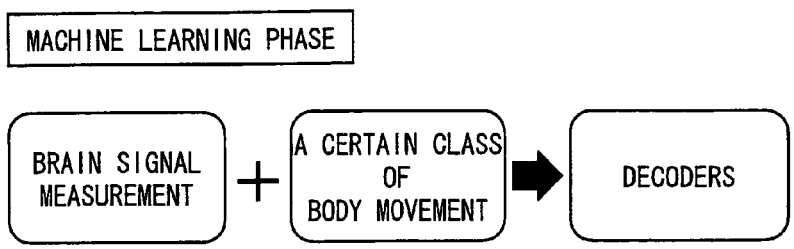
F I G. 4
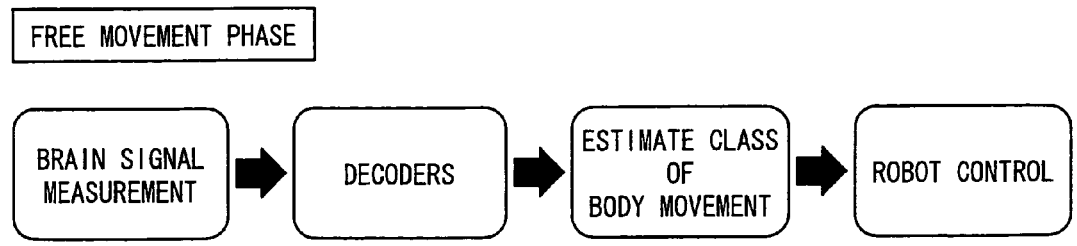

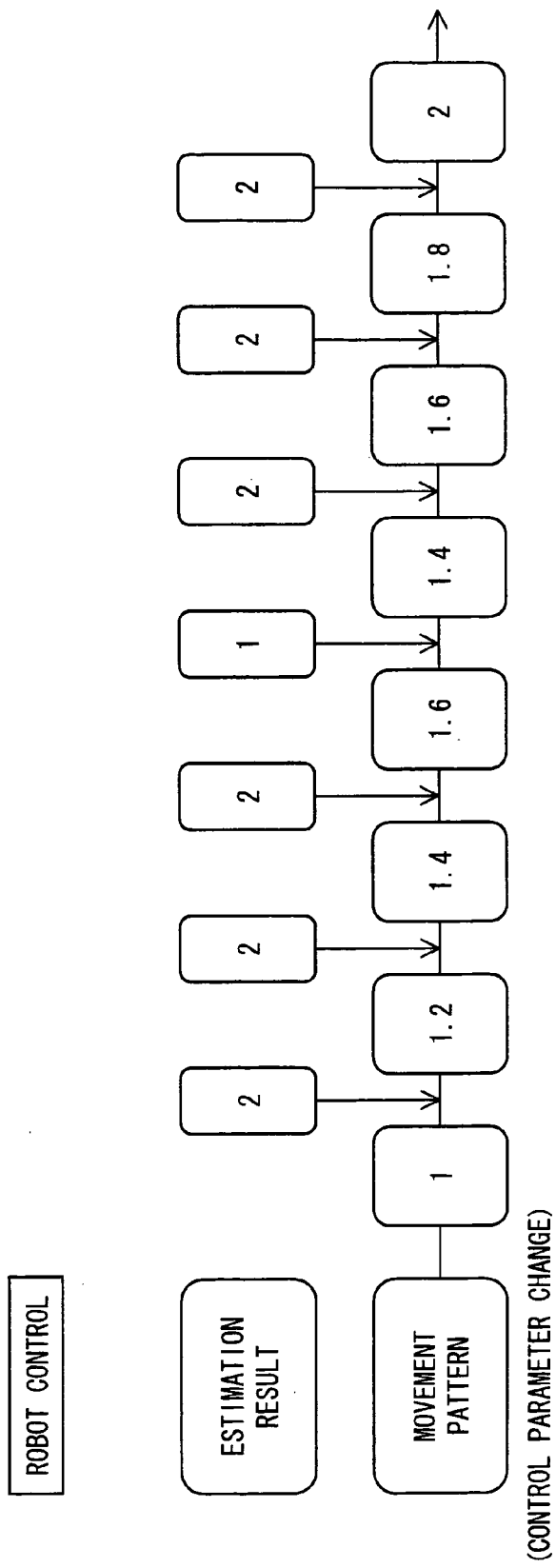

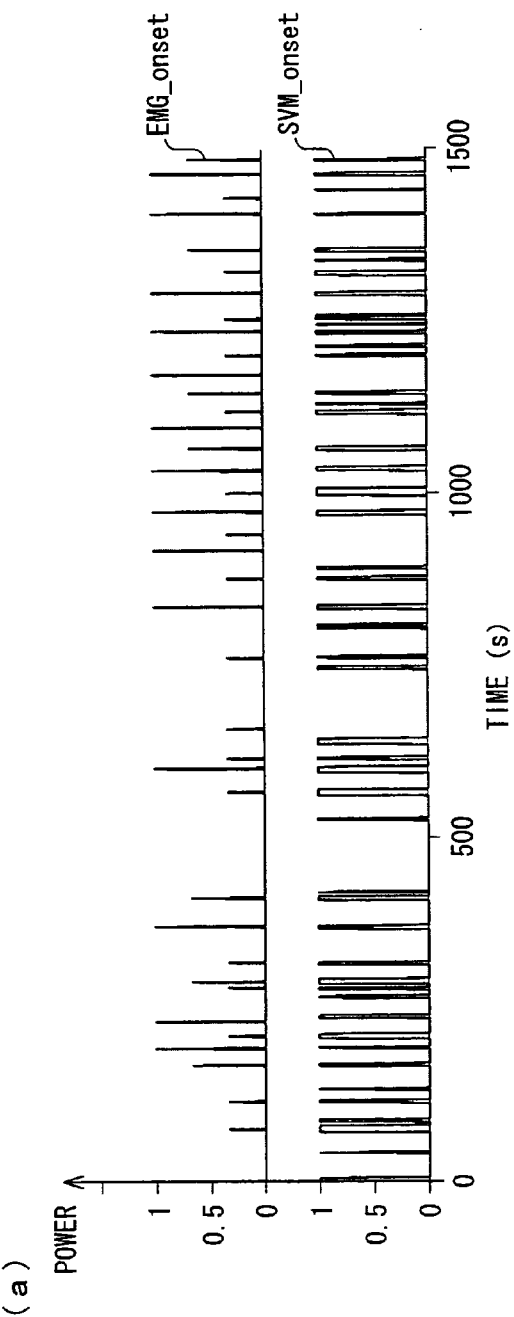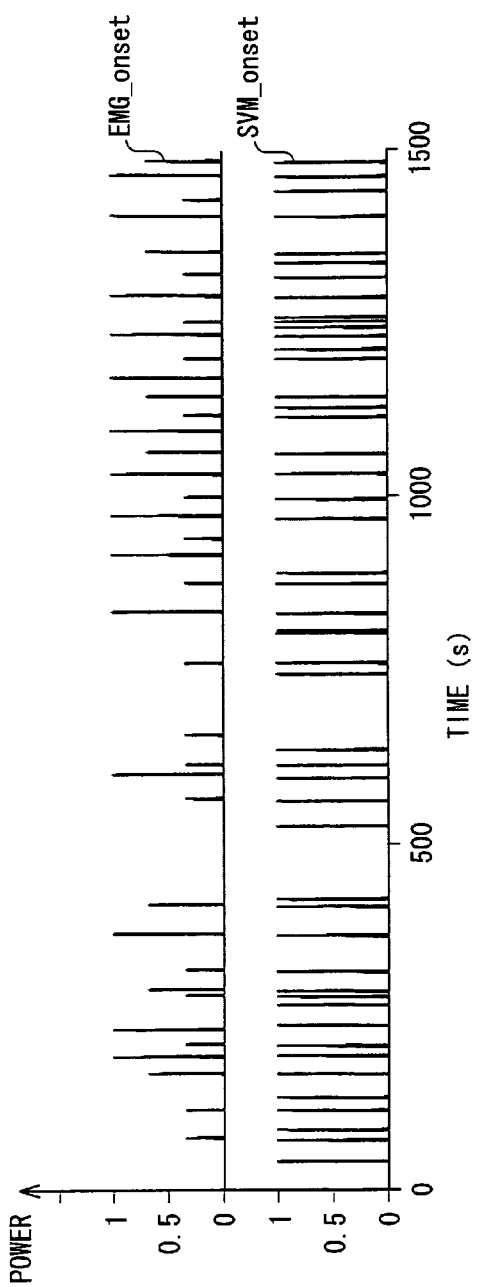
FIG. 6(a)
FIG. 6(b)

F I G. 7
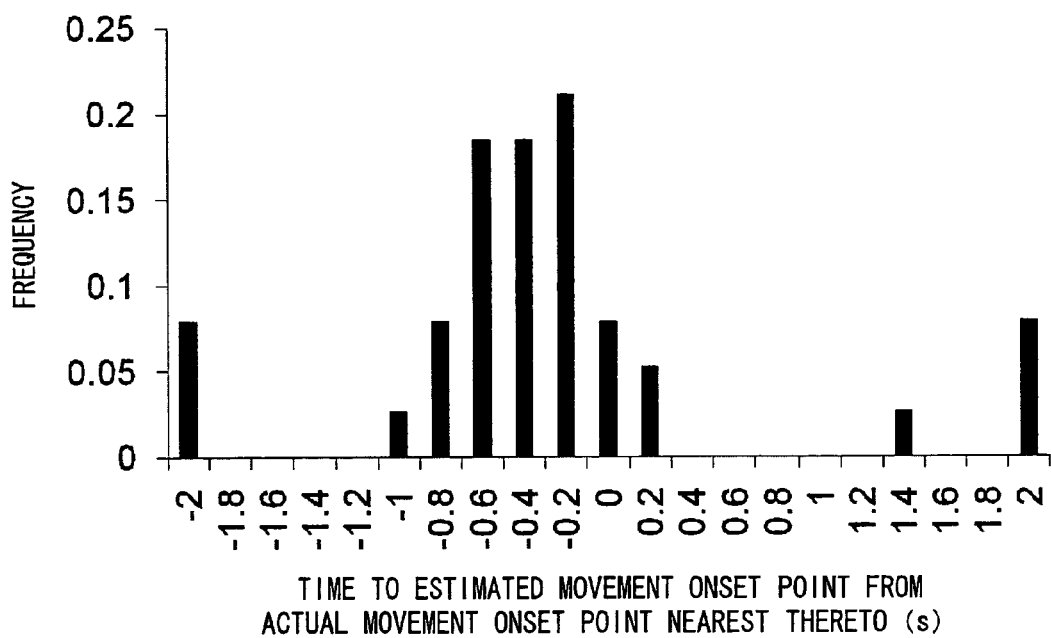

MACHINE CONTROL DEVICE, MACHINE SYSTEM, MACHINE CONTROL METHOD, AND RECORDING MEDIUM STORING MACHINE CONTROL PROGRAM

This Nonprovisional application claims priority under 35 U.S.C. §119(a) on Patent Application No. 2010-049814 filed in Japan on Mar. 5, 2010, the entire contents of which are hereby incorporated by reference.

TECHNICAL FIELD

The present invention relates to a machine control device, a machine control method, a machine control program, and a machine system using the machine control device, and a computer-readable recording medium in which the machine control program is stored. Each of the machine control method, the machine control program, the machine system, and the computer-readable recording medium realizes control of a machine such as a robot based on user's brain signals generated when the user performs or images a body movement.

BACKGROUND ART

Recently, brain-machine interface (BMI) technology has been developed as a means of rehabilitating motor function or a communication tool for severe locked-in syndrome patients suffering from spinal cord injury, amyotrophic lateral sclerosis, or the like. BMI is a technology to (i) estimate (decode), only from brain signals of a human, a body movement of the human which the human performs or images, (ii) and then control an external machine such as a computer, a robot, or the like based on the estimated movement. This technology enables a user to control the external machine such as a computer or a robot by using his brain to image (intend) a body movement, even if the user is totally impaired in motor function. This technology is realized by combining mainly three componential techniques (1) brain signal measurement, (2) brain information extraction, (3) external machine control based on extracted brain information. Recent intensive studies on (1) the brain signal measurement and (2) brain information extraction have improved BMI dramatically. In the following, the componential techniques are overviewed.

(Current Brain Signal Measurement)

The brain signal measurement methods can be divided into invasive measurement methods and non-invasive measurement methods. The non-invasive measurement methods do not require invasive treatment such as craniotomy and encompass: an EEG measurement in which electroencepharogram (EEG) is measured by using electrodes attached to scalp; an MEG measurement in which magnetoencephalogram (MEG) is measured; Near-infrared spectroscopy (NIRS); Functional magnetic resonance image (fMRI); and the like (see Non-Patent Literature 1).

On the other hand, the invasive measurement encompass: an ECoG measurement in which electrocorticogram (ECoG) is measured by using electrodes attached surgically to a brain surface inside cranium (see Non-Patent Literature 2); a multi-unit method in which activities of neurons are recorded individually by using a pinholder-like array of microelectrodes inserted into cerebral cortex (see Non-Patent Literature 3).

As brain signal measurement methods for controlling an external machine in real-time response to a change in brain signals, the EEG measurement, the MEG measurement, the ECoG measurement, and the multi-unit method are suitable among the methods listed above.

The non-invasive methods such as the EEG measurement and the MEG measurement are easy with little user burden, but can provide a smallest amount of brain information. Thus, the use of a non-invasive method has a difficulty of controlling a complicate movement of a machine, especially a complicate movement of a robot.

Meanwhile, the multi-unit method can provide a largest amount of brain information. However, the multi-unit method is susceptible to daily changes in the neurons, and therefore is so unstable that it is necessary to adjust the decoding of the brain signals everyday. Moreover, the multi-unit method becomes less sensitive after a long-term usage, because some of the microelectrodes become unusable after a long-term usage.

The ECoG measurement can provide an amount of brain information more than the non-invasive methods but less than the multi-unit method. The ECoG measurement is advantageous in that it can provide the brain signals stably. With these advantages, the ECoG measurement is expected as a clinically-applicable brain signal measurement for BMI. However, as mentioned above, the ECoG measurement is inferior to the multi-unit method in terms of the amount of brain information it can provide.

(Current Brain Information Extraction and External Machine Control)

Mainly, the brain information extraction methods can be divided into two methods: (a) reading from brain signals a body movement or language that a user (patient) performs or images; and (b) communicating intention of a user (patient) to a machine, by using brain signals as if switches, the brain signals being easy for the user to voluntarily control. The methods of type (a) requires a large amount of accurate brain information, thus are well developed for the multi-unit method in particular. Meanwhile, with the methods of type (b) the brain signal measurements such as the EEG method and MEG method which are incapable of providing much brain information can be utilized as effective communication tools by well designing the combination of a method of type (b) and such a brain signal measurement.

The method of type (a) directly reflects the user's intention to the external machine control. Thus, advanced control such as robot hand control can be carried out in real time. For example, Non-Patent Literature 4 describes a method in which a movement information of a monkey is extracted from an average firing rate of direction-selective neurons, and moves a robotic arm based on the movement information. With this method, the multi-unit method is adopted so as to measure the average firing rate of the direction-selective neurons (neurons for increasing firing frequency selectively at a particular movement direction and velocity) from a primary motor area of a monkey, and a direction and velocity of an upper limb movement of the monkey is estimated repeatedly from a firing pattern obtained from the measurement. Then, by sequentially connecting results of the estimation, a trajectory of the movement of the monkey is estimated. Non-Patent Literature 4 reported that this method could extract movement information from a brain of the monkey and thus allowed the monkey to move the robotic arm in a three-dimensional space as it desired.

Besides these arts, a method for two-dimensional control of a machine based on ECoG (see Non-Patent Literature 5), and a BMI technique using ECoG (see Patent Literature 1) have been proposed.

CITATION LIST

Patent Literature

Patent Literature 1
U.S. Pat. No. 7,120,486 (publication date Oct. 10, 2006)

Non-Patent Literatures

Non-Patent Literature 1
F. Nijboer, et al., 2008, "A P300-based brain-computer interface for people with amyotrophic lateral sclerosis", Clin Neurophysiol, 119, p. 1909-1916

Non-Patent Literature 2
E. C. Leuthardt, et al., 2006. "The emerging world of motor neuroprosthetics: a neurosurgical perspective", Neurosurgery, 59, p. 1-14 (especially p. 11-14)

Non-Patent Literature 3
L. R. Hochberg, et al., 2006. "Neuronal ensemble control of prosthetic devices by a human with tetraplegia", Nature, 442, p. 164-171.

Non-Patent Literature 4
M. Velliste, et al., 2008. "Cortical control of a prosthetic arm for self-feeding", Nature, 453, p. 1098-1101.

Non-Patent Literature 5
G. Schalk et al., 2008, "Two-dimensional movement control using electrocorticographic signals in humans", J Neural Eng, 5, p. 75-84

SUMMARY OF INVENTION

Technical Problem

These conventional brain information extractions and external machine controls are disadvantaged as follows.

The method as described in Non-Patent Literature 4, in which the direction and velocity of the upper limb movement is estimated from the firing pattern of the direction-selective neurons, makes it possible to estimate an upper limb movement from brain signals. However, in order to reproduce the trajectory of the upper limb movement accurately in the three-dimensional space with this method, it is necessary to use a highly-accurate and stable brain signal measurement and a well-trained monkey. As mentioned above, the multi-unit method is unable to provide highly-accurate and stable brain signals. Further, the method such as that described in Non-Patent Literature 4 is not applicable with the EEG measurement or the MEG measurement, which cannot provide a sufficient amount of brain information.

Non-Patent Literature 5 relates to a two-dimensional cursor control, meanwhile Non-Patent Literature 1 is directed to text input using event-related potential P300 of EEG. These arts cannot produce natural movement of machines, especially, a natural three-dimensional movement of robotic arms.

Moreover, because the methods of type (b) use the brain signals, that is, brain activity as if a switch to communicate with a machine, the user should carry out a long-term training to master operation of the machine in case the operation is complicated. Even after the user has mastered the operation, the operation of the machine takes a long time to complete, in case the operation is a complicated one such as robot operation.

It can be said that the abilities to perform complicate control of the external machine are conventionally dependent on how much amount of information can be obtained from the brain signals.

Further, the control of the external machine has not been studied enough, compared to the brain measurement and the continuous extraction of brain information from brain signals, which have been intensively researched.

The present invention was made in view of the aforementioned problems, and an object of the present invention is to provide a machine control device, a machine system using the same, a machine control method, a machine control program, and a computer-readable recording medium, each of which can provide machine control of making natural movement even if a limited amount of brain information is available, and each of which do not require a user thereof to carry out long-term training.

Solution to Problem

The present inventors studies the brain information extraction and external machine control method comprehensively, and as a result, made the present invention that can make a new progress in BMI.

In order to attain the object, a machine according to the present invention is a machine control device for controlling a machine based on brain signals of a user, comprising: an estimating section for estimating, from information of the brain signals, which one of body movements the user performs or images, the body movements going toward the first to nth body postures where n is an integer not less than 2, the estimating section performing the estimation on the body movement by using a first estimation model being prepared in advance by supervised learning with first training sets, each of the first training sets being a pair of the body movements and the information of the brain signals corresponding thereto; a correct rate estimating section for estimating from the information of the brain signals a correct rate indicating a probability that the estimation from the information of the brain signals by the estimation section is correct, the correct rate estimating section performing the estimation on the correct rate by using a second estimation model being prepared in advance by supervised learning with second training sets, each of the second training sets being a pair of the correct rate and the information of the brain signals corresponding thereto; a judging section for judging whether or not the correct rate thus estimated by the correct rate estimating section exceeds a threshold; and a machine control section for controlling the machine according to a result of the estimation performed by the estimation section, so as to change a posture of the machine between a first to nth postures through at least one intermediate posture therebetween, thereby the step of change from one of the first to nth posture to another of the first to nth postures including a plurality of substeps of change, the first to the nth postures being respectively associated with the first to nth body postures, wherein: the estimating section performs the estimation only if the judging section judges that the correct rate exceeds the threshold, and if the posture of the machine is not currently identical with the posture associated with the body posture toward which the body movement estimated by the estimating section goes, the machine control section changes the posture of the machine by performing a part of the substeps of change toward the posture associated with the body posture toward which the body movement estimated by the estimating section goes. A machine system according to the present invention comprises: the machine control device according to the present invention; and the machine controlled by the machine control device.

In order to attain the object, an method according to the present invention is a method for controlling a machine based on brain signals of a user, comprising: (i) performing first supervised leaning with first training sets, each of the first training sets being a pair of a body movement the user performs or images and information of the brain signals corresponding thereto, the first supervised learning creating a first estimation model for use in estimating, from the information of the brain signals, which one of the body movements the user performs or images, the body movements going toward the first to nth body postures where n is an integer not less than 2; (ii) calculating correct rates by performing plural times of estimation respectively from plural sets of the information of the body signals by using the first estimation model, the correct rates indicating probabilities that the respective results of the estimation are correct; (iii) performing second supervised learning with second training sets, each of the second training sets being a pair of the correct rate and the information of the brain signals corresponding thereto, the second learning creating a second estimation model for use in estimating a correct rate; (iv) estimating a correct rate from the information of the brain signals by using the second estimation model; (v) judging whether the correct rate estimated by the step (iv) exceeds a threshold or not; (vi) estimating by using the first estimation model, from the information of the brain signals, which one of the body movements the user performs or images, only if it is judged by the step (v) that the correct rate exceeds the threshold; and (vii) controlling the machine according to a result of the estimation performed by the step (vi), so as to change a posture of the machine between first to nth postures through at least one intermediate posture therebetween, thereby the step of change from one of the first to nth posture to another of the first to nth postures including a plurality of substeps of change, the first to the nth postures being respectively associated with the first to nth body postures, wherein: if the step (vi) performs the estimation and the posture of the machine is not currently identical with the posture associated with the body posture toward which the body movement estimated by the step (vi) goes, the step (vii) changing the posture of the machine by performing a part of the substeps of change toward the posture associated with the body posture toward which the body movement estimated by the step (vi) goes.

These configurations and method carry out estimation as to which one of a limited number of body movements (body movements going toward one of the first to nth body postures) the user performs or images, rather than such estimation on detailed information such as coordinates of final destination, a final angle of a joint, direction, velocity, etc. of the body movement that the user performs or images. Thus, these configurations and method make it possible to control a machine even with brain signals relatively small in brain information, for example, ECoG, EEG, EMG, etc.

Moreover, these configurations and method are arranged such that the machine is controlled to change the posture of the machine between the first to nth postures through at least one intermediate posture therebetween, thereby the step of change from one of the first to nth posture to another of the first to nth postures including a plurality of substeps of change. Thus, an error in the estimation on the body movement will appear as an "wobble" during the transition of the posture between the first to nth postures and such "wobble" does not make the whole movement unnatural, unlike a back-and-forth movement between the first to nth postures without passing through any intermediate postures. This make it possible control a machine to perform natural movement.

Moreover, the configurations and method are arranged such that the second estimation model for estimating a correct rate of the body movement estimation from the brain signal information is created by the learning with pairs of the brain signal information and the correct rates of the body movement estimation performed based on the first estimation model, and that a correct rate of body movement estimation is estimated from the brain signal information by using the second estimation model, and only if the correct rate thus estimated exceeds the threshold, the body movement estimation based on the first estimation model is performed, and then the machine is controlled according to the result of the body movement estimation based on the first estimation model. In this way, it is possible to avoid such erroneous operation that the posture of the machine is changed when the user does not perform nor image a body movement. Further, the body movement estimation is not performed when the machine is not to be controlled. This makes it possible to avoid doing unnecessary body movement estimation.

The sections of the machine control device may be realized on a computer by a machine control program. Further, by storing the machine control program in a computer-readable storage medium, it is possible to execute the machine control program on a computer.

Advantageous Effects of Invention

The present invention can provide a machine control device, a machine system using the same, a machine control method, a machine control program, and a computer-readable storage medium, each of which can control a machine to perform natural movement even with a limited amount of brain information, for example, in case ECoG is used as brain signals to detect, and which does not require a user to carry out a long-time training to master the control of the machine.

BRIEF DESCRIPTION OF DRAWINGS

FIG. 1 is a block diagram illustrating a configuration of a machine system according to one embodiment of the present invention.

FIG. 3 is a schematic diagram schematically illustrating an operation of the machine system according to the embodiment of the present invention. during a machine learning phase.

FIG. 4 is a schematic diagram schematically illustrating an operation of the machine system according to the embodiment of the present invention during a free movement phase.

FIG. 5 is a schematic diagram schematically illustrating how an electric prosthetic arm is controlled by a machine control method according to one embodiment of the present invention.

FIGS. 6(a) and 6(b) are graphs illustrating results of estimation on movement timing according to estimation methods of Comparative Examples.

FIG. 7 is a graph illustrating errors in the estimation on movement timing according to the estimation methods of the Comparative Example.

DESCRIPTION OF EMBODIMENTS

Figure 2:
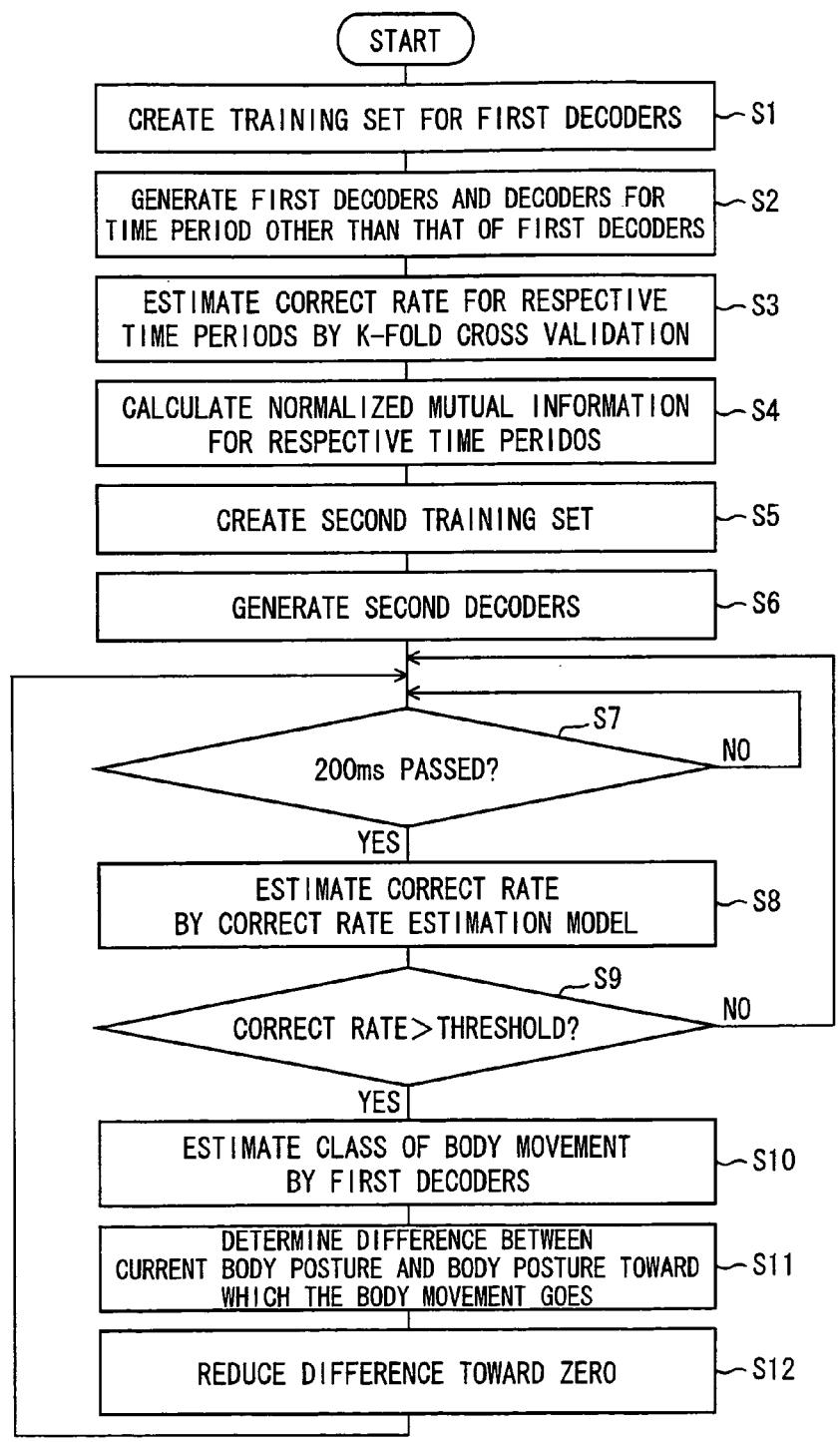
FIG. 2 is a flow chart illustrating a flow of a machine control method according to the embodiment of the present invention.

To begin with, an overview of one embodiment of the present invention is described.

One embodiment of the present invention is for causing an electric prosthetic arm (robotic arm) to perform a continuous movement. This embodiment carries out this by (i) extracting, from brain signals of a user, brain information corresponding to movement patterns between first to nth postures (where n is an integer not less than 2), (ii) combining these movement patterns sequentially, and (iii) causing the electric prosthetic arm to move according to the combination of the patterns (See FIG. 1).

In the embodiment of the present invention, brain signals of a user are measured when the user performs or images plural movement patterns in response to external trigger (machine learning phase). From the brain signals, features are extracted. Based on the correlation between the features and the movement patterns, decoders for estimating the movement patterns from the features are generated. The decoders are programs or operational circuits for carrying out computation to estimate only from brain signals a class of the movement, start timing of the movement, and the like. The decoders are generated by using a machine learning method such as a support vector machine (SVM), sparse logistic regression, and the like, which are used in a pattern recognizing program or the like. Here, two types of decoders are generated. First decoders are generated from brain signals obtained in a 1-second period right after the external trigger, by learning relationship between the brain signals and the movement patterns that the user performs or images. With the first decoders, a movement pattern that is newly performed or imaged is estimated from brain signals. Second decoders are generated from brains signals in three periods, namely a 1-second period right before the external trigger, a 1-second period right after the external trigger, and a 1-second period after the 1-second period right after the external trigger (that is, a period between 1 second after the external trigger and 2 second after the external trigger), by learning relationship between the brain signals and resultant mutual information. The resultant mutual information is calculated by normalizing mutual information provided from movement pattern estimation based on the brain signals from the three periods. The normalization normalizes the mutual information so that an average of the mutual information from these 3 periods is zero. With the second decoders, mutual information resulted from new brain signals can be estimated. The movement timing is estimated from whether or not the mutual information estimated by the second decoders exceeds a threshold value.

Thereafter, the learned movement pattern is carried out by the user with arbitrary timing and arbitrary length, it is judged whether or not the mutual information estimated by estimation model (second decoders) exceeds a threshold. If the mutual information exceeds the threshold value (in other words, when it comes to the timing of the movement), the first decoders discriminate only from brain signals the movement pattern that the user performs or images. For example, when the user performs or images a movement of hand closing, the second decoders estimate from brain signals that the user performs or images some sort of movement. The first decoders estimate from the brain signals that the user performs or images a movement of hand closing. This estimation is carried out at certain intervals. The movement of the electric prosthetic arm is controlled based on a result of the estimation. The movement of the electric prosthetic arm can be more natural by moving the electric prosthetic arm slowly, for example, by causing the electric prosthetic arm to slowly close its hand.

As to how to estimate, by using the decoders, which one of the body movements toward body postures the brain signals intend, and how to control the machine based on the estimation, it is an option to carry out these by putting the machine in a first posture corresponding to a first body posture, when the decoders estimate that the brain signals intends a body movement toward the first body posture, and by putting the machine in a second posture corresponding to a second body posture, when the decoders estimate that the brain signals intends a body movement toward the second body posture. This machine control method would lead to a significant error in the movement of the machine thereby making an unnatural movement of the machine, if the decoders led to an error in the estimation of the body movement. For example, in case this machine control method is applied such that the first body posture is a posture that the hand is open and the second body posture is a posture that the hand is close, it is carried out such that when it is estimated that the brain signals intend a body movement toward the first body posture, a robotic arm is caused to open its hand (the first posture corresponding to the first body posture), and when it is estimated that the brain signals intend a body movement toward the second body posture, the robotic arm is caused to close its hand (the second posture corresponding to the second body posture). In this case, for example, if the decoders leads to an error in the estimation of the body movement for a unit of time while the user is imaging the body movement of hand closing, the robotic arm performs such an unnatural movement that it transits from the posture that its hand is open to the posture that its hand is close, and then immediately returns to the posture that its hand is open.

On the other hand, the machine control device of the present invention controls the machine stepwise so that the machine moves between a first to an nth postures through at least one intermediate posture therebetween. Thus, even if an error occurred in the estimation on the body movement, the error would cause "wobble" corresponding to one step of the stepwise machine control in the movement between the first to nth posture, for example, in the movement from a first posture that the robotic arm (electric prosthetic arm) as the machine is opening its hand to a second posture that the robotic arm is closing its hand. Thus, as long as a majority of results of the estimation on the body movement is correct, the machine control device of the present invention makes it possible to perform the movement with wobble to one of the first to nth postures. For example, in case where the majority of the results of the estimation is that the movement goes toward the posture that "the hand is close", the robotic arm as the machine finally transits to the posture that "its hand is close", even though the movement is carried out with some wobble. That is, in the machine control device of the present invention, even if a correct rate of the estimation on the body movement is not 100%, the error merely causes "wobble" corresponding to one step of the stepwise machine control in the movement of the machine. As a result, the machine control device of the present invention can cause the machine to perform an intended movement relatively naturally. In this way, the present invention allows the machine to absorb, as "wobble" of the machine the error in the estimation on the brain information. This is a dramatic improvement over the conventional BMI.

It is said that body movements such as movements of human arms are combinations of some basic movements. Especially, body movements in daily life are composed of several fixed patterns. Therefore, when the machine control device of the present invention is applied to control a robot, such as a robotic arm, so as to cause the robot to emulate a daily-life body movement, it is important to cause the robot to perform such componential movements naturally and certainly. The present embodiment is to control a robot to move as a user intended, by combining a limited number of movements between one body posture to another, which movements are componential movement patterns of body movement such as arm movement or hand movement. Therefore, unlike the conventional BMI, the present embodiment can control the robot as long as brain information is available in an amount enough to estimate several body movement patterns. Thus, the present embodiment can realize practical robot control even with brain signals such as ECoG, EEG, and MEG, which cannot provide much brain information and are conventionally regarded as being unsuitable for robot control.

The machine control of the present invention estimates from the brain signals a movement that the user performs or images. Thus, the user is simply required to perform or image a movement that he/she wants to cause the machine to perform. Therefore, the user can master the operation of the machine with very little training. It has been confirmed that an almost-untrained subject could control a robotic arm in a three-dimensional space freely according to the present invention. The reduction in burden of training to the user can make the present invention applicable to a user (patient) such as an elderly human having a difficulty to carry out training. Compared with the conventional BMI techniques, the present invention is a BMI technique that is more clinically practical in terms of the burden of necessary training.

A machine control device and a machine system provided the same according to one embodiment of the present invention is described below referring to FIG. 1 to FIG. 12.

The machine system according to the present embodiment includes, as illustrated in FIG. 1, an electric prosthetic arm control device (a main part of the machine control device) 20, subdural electrodes 30, an electroencephalograph 40, a stimulus presenting device 50, and an electric prosthetic arm (machine) 60. The subdural electrodes 30 and electroencephalograph 40 are a part of the machine control device and constitute a brain signal measuring unit for measuring ECoG (brain signals) of a user. The electric prosthetic arm 60 is controlled by the electric prosthetic arm control device 20. The subdural electrodes 30 are to measure ECoG from an area including primary motor area in the brain of the user, and to output analog signals (brain signals) based on ECoG. It is preferable that the subdural electrodes 30 be placed in high density and to cover a large portion of the primary motor area. The subdural electrodes 30 are connected to the electroencephalograph 40 whereby the electroencephalograph 40 receives the analog signals of ECoG from the subdural electrodes 30. The electroencephalograph 40 transmits the analog signals of ECoG to the electric prosthetic arm control device 20 in real time. The stimulus presenting device 50 presents a stimulus and at the same time transmits a trigger to the electric prosthetic arm control device 20 via the electroencephalograph 40.

The electric prosthetic arm 60 is a robot that emulates a human arm, and is capable of taking plural postures (first to nth postures) that correspond to plural postures (first to nth body postures) that the human arm may take.

The electric prosthetic arm control device 20 controls the electric prosthetic arm 60 based on the user's brain signals, and includes an A/D (Analog-digital) converter 1, a data clipping section 2, a feature extracting section (brain information extracting section) 3, a decoder generating section 4, first decoders (estimating section) 5, second decoders (correct rate estimating section) 6, a judging section 7, and an electric prosthetic arm control section (machine control section) 8.

The A/D converter 1 converts the analog signals of ECoG into digital signals (ECoG data) of ECoG, the analog signals of ECoG having been transmitted from the electroencephalograph 40 to the electric prosthetic arm control device 20.

The data clipping section 2 clips ECoG data of a predetermined period from the ECoG data supplied from the A/D converter 1. The feature extracting section 3 extracts features (information of the brain signals) from the ECoG data of the predetermined period thus clipped by the data clipping section 2. The features may be, for example, powers of ECoG at the respective subdural electrodes 30 in plural frequency bands. Based on a second estimation model, the second decoders 6 predict accuracy (normalized mutual information) of estimation carried out based on the features extracted from the brain signals by the feature extracting section 3. The judging section 7 judges whether or not an output (the normalized mutual information thus predicted) of the second decoders 6 exceeds a threshold. If the output exceeds the threshold (Yes), the judging section 6 supplies to the first decoders 5 the features extracted by the feature extracting section 3. On the other hand, if the output does not exceed (No), the judging section 7 sends to the electric prosthetic arm control section 8 a signal (a signal of No) indicating that the output does not exceed the threshold. The threshold is based on the second estimation model that is created by the decoder generating section 4 in advance.

Based on a first estimation model, the first decoders 5 estimate, from the brain signal information, which one of body movements the user performs or images, the body movements transferring the body posture toward the first to nth posture (where n is an integer not less than 2). The first estimation model is created by the decoder generating section 4 in advance.

Figure 12:
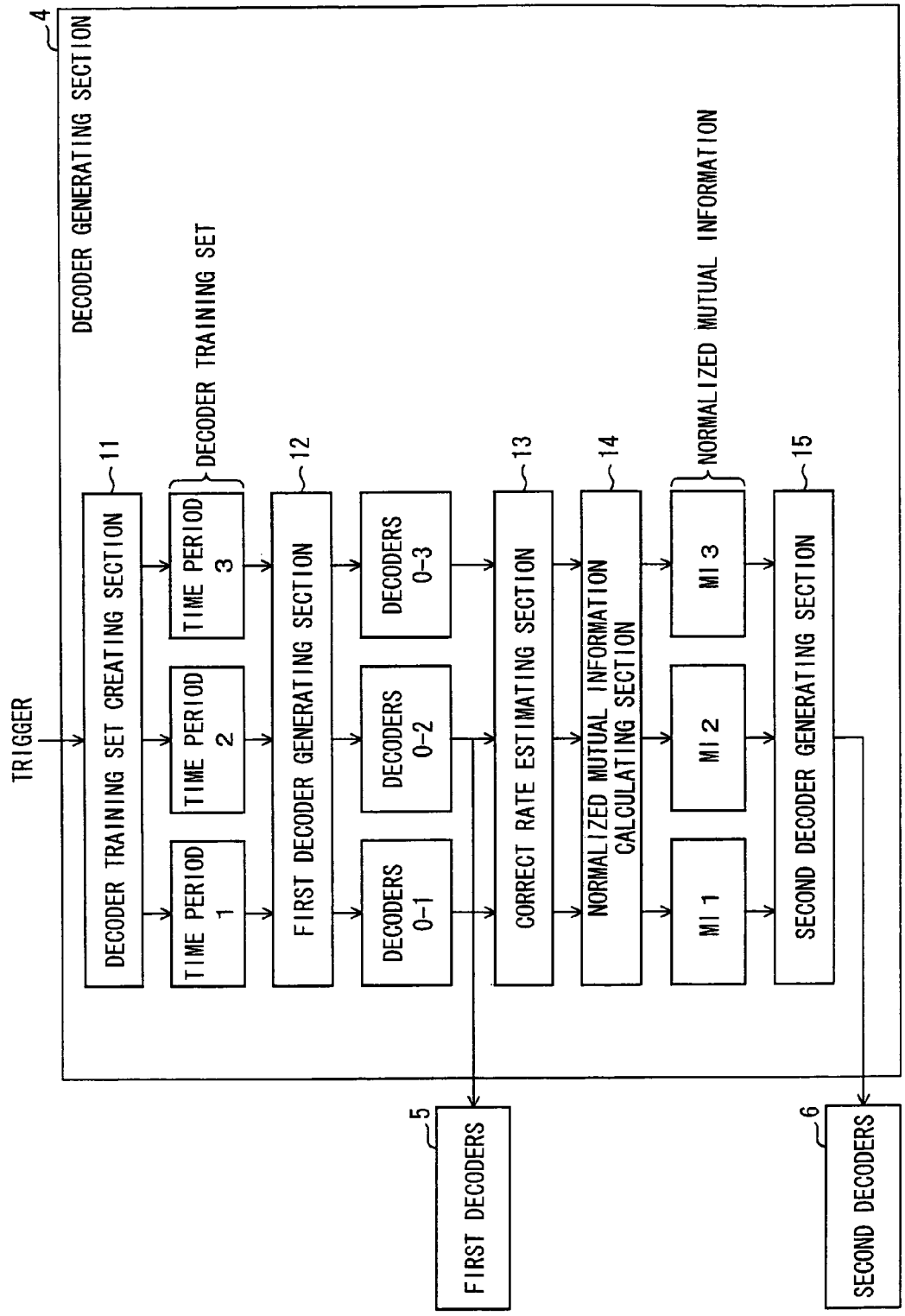
FIG. 12 is a view illustrating a decoder generating section of a machine system according to one embodiment of the present invention in more details.

The decoder generating section 4 is activated if the feature extracting section 3 receives both of the trigger and the brain signal labeled with the body movement that the user performs or images. The input of the trigger to the electric prosthetic arm control device 20 is notified from the feature extracting section 3 to the decoder generating section 4. The decoder section 4, as illustrated in FIG. 12, includes a decoder training set creating section 11, a first decoder generating section 12, a correct rate estimating section 12, a normalized mutual information calculating section 14, and a second decoder generating section 15.

By the decoder training set creating section 11, the ECoG data clipped by the data clipping section 2 is divided into three data sets for 3 one-second time periods based on timing correlation with the trigger. Then, the decoder training set creating section 11 extracts features from the data set for each time period and creates training sets (first training sets) respectively for the time periods (in FIG. 12, the training sets for the time periods are respectively labeled as "time period 1", "time period 2", and "time period 3"). Each training set is a pair of features (brain signal information) and a body movement that the user performs or images.

As the first estimation model, the first decoder generating section 12 generates decoders for the respective periods, namely, decoders 0-1 for the first time period, decoders 0-2 for second time period, and decoders 0-3 for third time period, by supervised learning that uses the training sets, each of which is a pair of the features (brain signal information) and the body movement that the user performs or images.

The correct rate estimating section 13 creates pairs of answers (classes of body movements that the user actually performs or images) and estimated values (values each indicating a class of movement that is estimated by using the first decoders 5), in order to estimate by k-fold cross validation a -correct rate of estimation performed by the first decoders based on the features (brain signal information).

The normalized mutual information calculating section 14 calculates mutual information of each time period from the pairs of the answers and estimated values which pairs are created by the correct rate estimating section 13. Then, the normalized mutual information calculating section 14 normalizes the mutual information so that an average of the mutual information of the time periods is zero.

The second decoder generating section generates the second decoders 6 by supervised learning that uses training sets (second training sets) for the time periods. Each of the second training sets is a pair of the features and normalized mutual information.

According to a result of the estimation performed by the first decoders 5, the electric prosthetic arm control section 8 controls the posture of the electric prosthetic arm 60 stepwise so that the electric prosthetic arm 60 moves between the first to nth postures through at least one intermediate posture therebetween, the first to nth postures corresponding to the first to nth body postures of the body movement respectively. When the estimation is performed by the first decoders 5 and the current posture of the electric prosthetic arm 60 is different from a posture that corresponds to a body posture toward which the first decoders 5 estimate the body movement goes, the electric prosthetic arm control section 8 transfers the posture of the electric prosthetic arm 60 by one step toward the posture that corresponds to the body posture toward which the first decoders 5 estimate the body movement goes. If the electric prosthetic arm control section 8 receives a NO signal from the judging section 7, the electric prosthetic arm control section 8 maintains the posture of the electric prosthetic arm 60 as it is now. If the electric prosthetic arm 60 has been maintained in one posture for a certain period of time, the electric prosthetic arm control section 8 returns the electric prosthetic arm 60 to a neutral position (corresponding to a neutral position in which the electric prosthetic arm is relaxed).

In the following, a machine control method according to one embodiment of the present invention referring to FIG. 2 is described.

To begin with, the machine control method according to the present embodiment performs machine training in steps Si to S5.

In order to perform the machine training, the stimulus presenting device 50 presents a stimulus and at the same time, sends a pulse signal to the data clipping section 11 via the electroencephalograph 40 and the A/D converter 1. The pulse signal indicates a timing at which the stimulus is presented. In response to the stimulus presented by the stimulus presenting device 50, the user performs or images plural classes of body movements (movement tasks) that moves from the first to nth postures. This is carried out plural times for each class of body movement. When the user carried out each movement task, an observer inputs, to the electric prosthetic arm control device 20 from an input section 10, a class of the movement task that the user performs or images. The data clipping section 2 clips ECoG data of a predetermined period from ECoG data obtained while the user performs or images the movement tasks, and then the data clipping section 2 labels the clipped ECoG data with a label of the body movement that the user performs or images in the movement each task (i.e., the data clipping section 2 associates the clipped ECoG data with the body movement).

The stimulus may be a sound stimulus, light stimulus, or the like. Sound stimulus is more preferable. The number of classes of body movements to be performed or imaged for the machine training is not particularly limited and may be 2 to 5 classes. The classes of the body movements may be, for example: "closing a hand" movement from a neural posture in which the hand is relax, to a posture the hand is close; "opening a hand" movement from the neutral posture to a posture in which the hand is open; "pinch something with fingers" movement from the neutral posture to a posture in which something is pinched with two fingers; "bending elbow" movement from the neutral posture to a posture in which an elbow is bent; and "straightening elbow" movement from the neutral posture to a posture in which the elbow is fully straightened. The plural classes of the body movement can be selected arbitrarily, and may be selected in consideration of which movement of the electric prosthetic arm 60 are desired, because the plural classes of the body movement forms movement of the electric prosthetic arm 60. By way of example, the present embodiment is arranged such that the movement tasks are carried out with the 5 classes of body movement listed above.

When the body movement as the movement task is performed or imaged, and both of the trigger and the brain signal labeled with the label of the body movement is inputted to the feature extracting section 3, the decoder generating section 4 is activated, and the decoder training set creating section 11 creates training set data that is to be used by the first decoder generating section 12 (S1). The training set data includes pairs of (i) data indicative of classes of body movements that the user performed or imaged (i.e., classes of body movements that the user performed or imaged from among predetermined plural classes of body postures), and (ii) data indicative of the features obtained when the user performed or imaged the body movements corresponding thereto. The training set data is created referring to (i) the features obtained by the feature extracting section 3 at each electrode for the respective frequency bands during the three time periods, respectively, and (ii) the classes of the body movements inputted by the operator (or observer) during the periods for which the ECoG data were clipped.

Next, by the supervised learning in which all the training set data is used, the first decoder generating section 12 generates decoders 0-1 to 0-3 which is based on the first estimation model for estimating, from features (brain signal information) of ECoG data, which one of the body movements the user performs or images, each of the body movements putting the body into one of the body postures (S2). The decoders 0-1 to 0-3 are generated for the three time periods respectively. The decoders (decoders 0-2) for the second time period (time period 2) is used as the first decoders 5. As to the first estimation model, the present invention is not limited to a particular technique and may adopt a classifier (discriminator) such as support vector machine, neural network, Gaussian process regression modified for classification, sparse logistic regression modified for classification, etc. For more accurate classification, it is preferable to use a classifier as the first estimation model.

Next, based on (i) features of user's ECoG data obtained when the user performed or imaged the same movement task again, and (ii) a movement estimated from the features, the correct rate estimating section 13 estimates for each time period a correct rate (generalization capability) of a result of the estimation performed with the first decoders 5 (S3). How to calculate the correct rate is not particularly limited, but can be easily performed by using k-fold cross validation.

By the normalized mutual information calculating section 14, the mutual information between the body movement estimated from the features extracted from the brain signal of the user and the body movement that the user actually performs or images is calculated for each time period, and normalized such that an average of the mutual information for the time periods becomes zero (S4). The mutual information thus normalized is the normalized mutual information.

From the normalized mutual information for the time periods and the features thus obtained for the time period, the second training set is created (S5). Based on the second training set, the second decoder generating section 15 generates the second decoders 6 (S6). The second decoders 6 makes it possible to avoid such false operation that the posture of the electric prosthetic arm 60 is changed even though the user does not perform nor image a body movement.

The estimation model used as the second decoders 6 is not limited to a particular technique, and may be Gaussian process regression, linear discriminant analysis, sparse logistic regression, or the like. The present embodiment adopts Gaussian process regression as the estimation technique for the normalized mutual information, because the Gaussian process regression allows highly accurate estimation even with training data that is collected a small number of times. It should be noted, however, that the present invention is not limited to Gaussian process regression.

Next, the user performs or images a body movement freely. Meanwhile, the data clipping section 2 clips ECoG data for 1 second (from 1 second before to present) at intervals of a predetermined time period and the feature extracting section 3 extracts from the ECoG data of each one second period, the features (powers, or the like) per electrode for the respective frequency bands. The predetermined time period is not particularly limited, but is 200 milliseconds in the present embodiment.

Then, at intervals of 200 milliseconds (predetermined time period), the estimation and control of S8 to S11 are carried out in real time. That is, in the present embodiment, it is judged whether or not the time period of 200 milliseconds has been passed (S7). The judgment is repeated until the time period of 200 milliseconds is passed. Then, after the time period of 200 milliseconds is passed, the process goes to S8.

Next, at S8 and S9, the second decoders 6 and the judging section 7 estimate, by using the Gaussian process regression, whether or not this present time is a timing of performing a movement (i.e., whether or not at this present time the electric prosthetic arm is required to perform a movement). That is, the second decoders 6 and the judging section 7 search for a period that is, with high correct rate, a timing of performing the movement. In other words, the second decoders 6 estimate the correct rate (normalized mutual information) from the features of the ECoG data for 1 second, by the estimation model prepared at S6 (S8).

Then, the judging section 7 judges whether the correct rate thus estimated exceeds a certain threshold or not (S9). If the correct rate thus estimated exceeds a certain threshold, it is estimated that a period between the present time and 1 second before the present time is a period suitable for the estimation of the class of movement (this period corresponds to a period when the user performs or images a movement). Then, the process moves to S10 for the estimation performed by the first decoders 5. On the other hand, if the correct rate thus estimated does not exceed the certain threshold, it is estimated that the period between the present time and 1 second before the present time is a period unsuitable for the estimation of the class of movement (this period corresponds to a period when the user does not perform or image a movement). Thus, the estimation performed by the first decoders 5 is not carried out, and a signal indicating that the user is not performing or imaging a movement is sent to the electric prosthetic arm control section 8. Then, the process returns to S7 and is repeated for the next cycle. Thus, the estimation on the class of movement is carried out only for periods estimated as being suitable for the estimation of the class of movement (only the periods in which the correct rate thus estimated (normalized mutual information) exceeds the certain threshold). The estimation on the class of movement is carried out by applying the first decoders 5 to ECoG data of the periods. The threshold can be arbitrarily adjusted during real-time control of the electric prosthetic arm 60. By adjusting the threshold, the detection of the timing of performing a movement can be adjusted in terms of sensitivity and specificity. For example, the threshold may be a value approximate to 0.

Next, by the first decoders 5 prepared at S2, the class of the body movement that the user performed or imaged is estimated from the features of the ECoG data (S10).

Next, the electric prosthetic arm control section 8 controls the electric prosthetic arm 60 in real time based on the body posture toward which the body movement, which the first decoders 5 estimated at S10 the user performed or imaged, goes (S11 to S12).

The electric prosthetic arm control section 8 performs this control in which the posture of the electric prosthetic arm 60 is changed stepwise between a first to nth postures (where n is an integer not less than 2) via an intermediate posture(s) therebetween, the first to the nth postures corresponding respectively to the first to nth body postures. In this embodiment, the electric prosthetic arm control section 8 performs this control as a p-stage control (where p is an integer not less than 2) in which the posture of the electric prosthetic arm 60 is changed stepwise in a direction from the first posture (corresponding to the first body posture of the user) to the second posture (corresponding to the second body posture of the user) via an intermediate posture(s) therebetween. The change in the posture of the electric prosthetic arm 60 is carried out stage by stage via the p stages (substeps) (where p is an integer not less than 2) through the intermediate posture(s) between the first posture and the second posture, which respectively correspond to the first body posture and the second body posture of the user. The stepwise change in the posture of the electric prosthetic arm 60 is controlled by changing a control parameter indicative of the posture of the electric prosthetic arm 60, from a current value toward a value corresponding to the body posture toward which the estimated body movement goes (for example, the estimated body movement is to close the hand, the body posture targeted by the estimated body movement is the closed hand). The control parameter is gradually changed by a constant value at a time, the constant value corresponding to one stage of the change in the posture. (The constant value=$1/p \times D$ where D is different between the value of the control parameter corresponding to the first body posture and the value of the control parameter corresponding to the second body posture.)

The number of stages p is not particularly limited, but is preferably in a range of 3 to 5. For example, assume that the value of the control parameter corresponding to the first body posture is 1, the value of the control parameter corresponding to the second body posture is 2, and p is 5, the change in the posture of the electric prosthetic arm 60 is carried out by changing the control parameter of the electric prosthetic arm 60 by constantly 0.2 (the constant value corresponding to one stage) at a time from the current value toward the value corresponding to the body posture toward which the estimated body movement goes.

More specifically, the present embodiment is arranged as follows. The electric prosthetic arm control section 8 calculates a difference between the posture of the electric prosthetic arm 60 corresponding to the body posture toward which the estimated body movement goes and the current posture of the electric prosthetic arm 60 (S11). Then, the electric prosthetic arm control section 8 changes the posture of the electric prosthetic arm 60 in such a manner that the difference is reduced toward 0 by the constant value corresponding to the one stage (S12). After that, the time period is reset to 0 and the process returns to S6. Via this process, the electric prosthetic arm 60 performs a movement, i.e. a change in its posture (change in the control parameter) like the movement pattern as illustrated in FIG. 5. If the difference is 0 at S11, the electric prosthetic arm control section 8 maintains the posture of the electric prosthetic arm 60 as such.

The multi-stage control of the electric prosthetic arm 60 as such increases the number of steps to complete the change in the posture from the first posture to the second posture or vice versa. However, this arrangement makes it possible that even if the first decoders 5 made an error in the estimation of the class of the movement, the electric prosthetic arm 60 can change its posture toward the intended posture by going through the steps as long as the probability of making correct estimation of the movement is above chance.

The present embodiment is arranged such that the change in the control parameter is constant at all the stages. However, the change in the control parameter may be various over the stages. Moreover, it may be arranged such that, in a special case (for example, in case the body posture toward which the estimated body movement goes is the first body posture), the change in the control parameter in carried out in stages more divided than the p stages, while the change in the control parameter is carried out in the p stages in the other cases.

[Variations]

The present invention is not limited to the embodiments described above, and can be modified in various ways within the scope of the claims and the technical scope of the present invention encompasses any embodiments obtainable from appropriate combinations of the technical means disclosed in different embodiments.

For example, the machine control method of the embodiment may be arranged such that the movement of the electric prosthetic arm 60 according to the result of the estimation based on the brain signals is controlled to change in more stages by increasing p in case the estimation on the body movement estimates a rapid change of body movement based on a history of movements (previous movements) of the electric prosthetic arm 60. In general, a human does not rapidly repeat the movement of "closing his hand" and the movement of "opening his hand" in such short cycle of 200 ms. Thus, if the result of the estimation performed by the first decoders 5 is unnatural in consideration of the history of the movements of the electric prosthetic arm 60, the number of p is increased to reduce an influence of such an unnatural result of the estimation. This further alleviates the influence of the "wobble" of the electric prosthetic arm 60, thereby performing the movement of the electric prosthetic arm 60 more natural.

Moreover, while the system of the embodiment uses the ECoG as the brain signals, the present invention is applicable to a wide variety of brain signals and may use brain signals other than ECoG as the brain signals. For example, EEG, MEG, and the brain signals obtained by the multi-unit method may be used. It is preferable to use ECoG as the brain signals because ECoG is excellent in stability to allow stable machine control. As to the feature, the present invention is applicable to a wide variety of features and may be applied to various features other than the kind of the features exemplified in the embodiment (powers per electrode for the respective frequency bands). It is preferable to extract as the features the powers of the brain signals for the respective plural frequency bands, because this can obtain more brain information thereby making it possible to perform more accurate movement estimation and machine control.

The sections of the electric prosthetic arm control device 20 and the steps of the embodiment can be realized by causing a computing means such as a CPU to execute a program stored in a recording means such as a ROM (Read Only Memory) or Ram, and to control input means such as a key board, output means such as a display device, and/or communication means such as an interface circuit. Thus, the functions and processes of the electric prosthetic arm control device 20 according to the present embodiment can be realized merely by a computer reading out the program from a recording medium in which the program is stored, and executing the program thus read out. By recording the program in a removal recording medium, it is possible to realize the functions and processes on arbitrary computers.

The recording medium as a program medium may be a memory (not illustrated) for microcomputer process, such as ROM. As an alternative, the program medium may be a recording medium readable via a program reading device (not illustrated) as a peripheral storage device, to which the recording medium is inserted and read.

The program stored in the recording medium of any of these kinds is preferably executed by a microprocessor accessed to the program. Further, it is preferable that the program is read out and downloaded in a program storage area of the microcomputer, and then executed by utilizing the program storage area. A program for carrying out the download is stored in the main device in advance.

The program medium may be a storage medium detachable from the main device and storing the program as a storage medium, such as tapes, such as magnetic tapes and cassette tapes; discs such as magnetic discs (FD (flexible discs), hard discs, etc.), and discs such as CD (compact disc), MO (magneto-optical disc), MD (MiniDisc), and DVD (digital versatile disc); card storage media, such as IC (integrated circuit) cards and optical cards; and semiconductor memories, such as mask ROMs, EPROMs (erasable programmable ROMs), EEPROMs (electrically erasable programmable ROMs), and flash ROMs.

Moreover, if the system is connectable to a computer network such as the Internet, the recording medium may be a transitory medium storing the program such that the program is downloaded from the communication network.

Further, if the program is downloaded from the communication network as above, it is preferable that the program for carrying out the download is stored in the main device in advance, or installed from another recording medium.

In the following a more specific Example of the present embodiment is described. It should be noted that the following method and configuration are merely examples to which the present invention is not limited.

Example 1

In the present Example, the user was a patient suffering from intractable pain after right thalamic hemorrhage. The patient was implanted with sixty of subdural electrodes 30 in his right sensorimotor area for sensorimotor area stimulation therapy. With the patient informed consent, the patient carried out machine learning and task on free movement.

[1. ECoG Measurement]

In the present Example, the patient was implanted with the sixty of subdural electrodes 30 on his brain surface by craniotomy procedure. The subdural electrodes 30 thus implanted were made by Unique Medical. Co., (Tokyo, Japan) and arrayed in matrix. The subdural electrodes 30 are placed mainly in his primary motor area based on somatosensory evoked potential (SEP) and anatomical positional relationship. Each of the subdural electrodes 30 was a disk of 3 mm in diameter. The subdural electrodes 30 were arrayed with 7 mm intervals between each center thereof.

In the present Example, the electric prosthetic arm control device 20 was a computer system (National Instruments Texas, USA; NI PXI-6225) provided with a hard disc as mentioned above in which an electric prosthetic arm control program of the present invention was stored.

In the present Example, the electroencephalograph 40 was a digital electroencephalograph for clinical use (Nihon Koden Co., Tokyo, Japan; EEG 2000). The digital electroencephalograph had functions of extracting a particular frequency component from inputted analog signals of ECoG by using a low-pass filter, performing A/D conversion (analog-digital conversion) of the extracted particular frequency component by an A/D converter so as to generate digital signals of ECoG, and storing in a memory device the digital signals as clinical data. Further, the present Example was arranged such that the A/D conversion was performed with a sampling rate of 1 kHz and time constant of 2.0 seconds, and the low-pass filter had a cut-off frequency of 300 Hz. The brain signals were supplied to the electric prosthetic arm control device 20 in such a way that digital signals of ECoG were converted into analog signals by D/A conversion by the electroencephalograph 40, and the analog signals of ECoG thus obtained were transmitted to the A/D converter 1 of the electric prosthetic arm control device 20, where the analog signals of ECoG were converted into digital signals of ECoG by the A/ D converter 1.

In the Present Example, the A/D converter 1 had a sampling rate of 1 kHz and time constant of 2.0 seconds. Moreover, in the present Example, the A/D converter 1 had a low pass filter for filtering off, from the analog signals, components other than low frequency components, and the low pass filter had a cut-off frequency of 300 Hz.

[2. Feature Extraction and Decoder Generation]

The electric prosthetic arm control device 20 used an electric prosthetic arm control program that utilized a numerical analysis program "MATLAB®" (the MathWorks, Inc.; Natick, Mass., USA". By the electric prosthetic arm control program the electric prosthetic arm control device 20 performed real-time signal process of the digital data (ECoG data), clipping of the ECoG data, feature extraction, decoder generation, novel (ECoG-based) movement estimation, novel electric prosthetic arm control, etc.

[2.1. First Machine Learning Phase]
[2.1.1. Collection of ECoG Data in Resting State]

An operator of the electric prosthetic arm control device 20 instructed the patient to maintain a rest state for 50 seconds, who was implanted with the subdural electrodes 30 on his brain surface. While the patient kept the rest state as instructed, the A/D converter 1 outputted ECoG data of the rest state to the data clipping section 2 and the data clipping section 2 clipped the ECoG data of the rest state per 1 second period and stored the clipped ECoG data in a recording section (not illustrated) of the data clipping section 2. By this, the recording section of the data clipping section 2 recorded fifty times 1-second ECoG data of the rest state.

After that, the feature extracting section 3 performs fast fourier transformation (FFT) of each 1-second ECoG data of the rest state per each electrode for respective plural frequency bands, thereby calculating powers (square of amplitude) of ECoG in the plural frequency bands per electrode. There is not particular limitation as to the number of the frequency bands and ranges of the frequency bands. In the present Example, the following three frequency bands were used: 1 to 8 Hz; 8 to 25 Hz; and 80 to 150 Hz. The number of the frequency bands and ranges of the frequency bands can be arbitrarily selected. For example, the following three frequency bands may be used: 1 to 8 Hz; 25 to 40 Hz; and 80 to 150 Hz.

Per each electrode the feature extracting section 3 averages the powers of ECoG from the fifty times recording for the three frequency bands, respectively. Thereby, the feature extracting section 3 created data indicating an average power of ECoG for each combination of the sixty subdural electrodes and the three frequency bands. The feature extracting section 3 recorded the data as ECoG data of the rest state in a recording section (not illustrated) of the feature section 3.

[2.1.2. Creation of First Training Data]

Next, the patient carried out movement tasks by moving his upper limb in response to a stimulus presented by the stimulus presenting device 50. The upper limb was an arm contralateral to that side of the brain to which the subdural electrodes 30 were implanted. In the present Example, the stimulus presenting device 50 was an audio stimulus presenting device ("ViSaGe" made by Cambridge Research Systems Ltd., Rochester, UK) that presents three sounds "Pi", "Pi", "Po" with 1-second intervals as the audio stimulus. That is, the stimulus presenting device 50 in the present Example repeated cycles of 3-second stimulating operation in which the sound "Pi" is presented at the beginning of each cycle, the sound "Pi" is presented 1 seconds after the beginning of each cycle, and the sound "Po" is presented 2 seconds after the beginning of each cycle. The patient performed one class of body movement in response to the sound "Po" presented lastly in every cycle. The one class of body movement was selected by the patient himself from among plural classes of body movements that change his body posture from one to another (in other words, body movements to target another body posture). In the present Example, the plural classes of body movements were the following three classes: a body movement of "closing a hand" to change the body posture from its neutral posture to the body posture of "the hand is close"; a body movement of "opening a hand" to change the body posture from its neutral posture to the body posture of "the hand is open"; and a body movement of "pinch something with fingers" to change the body posture from its neutral posture to a posture to pinch something with his thumb finger, first finger, and second finger.

The stimulus presenting device 50 was configured to output a trigger to the electroencephalograph 40 at the same time the stimulus presenting device 50 presented the sound "Po". The trigger was a pulse signal indicative of timing when the stimulus was presented. The pulse signal was sent to the data clipping section 2 via the electroencephalograph 40 and the A/D converter 1 in sync with the ECoG signals obtained when the stimulus presenting device 50 presented the sound "Po". The data clipping section 2 processed the pulse signal. In the present Example, the pulse signal was TTL (Transistor-Transistor-Logic) signal. In the electric prosthetic arm control device 20 of the present Example, the data clipping section 2 obtained the ECoG data from the A/D converter 1 every 100 ms, and clipped ECoG data of a period between −1 second and +2 second with respect to the time at which the TTL signal for the sound "Po" was detected (hereinafter, this period is referred to as "−1 second to +2 second period"). Next, the feature extracting section 3 divided the −1 second to +2 second period into three periods, namely "−1 second to 0 second period", "0 second to 1 second period", and "1 second to 2 second period". Then, for each electrode, the feature extracting section 3 calculated powers of the ECoG data in these periods for the three frequency bands (1 to 8 Hz, 8 to 25 Hz, and 80 to 150 Hz), respectively as did for the resting state. Furthermore, the feature extracting section 3 normalized the powers of the ECoG data of these periods per electrode for the respective frequency bands by referring to the powers of the resting state recorded in the recording section of the feature extracting section 3 (i.e., the powers of the ECoG data of these periods per electrode for the respective frequency bands were normalized as relative values based on the power of the resting state). The normalized values were regarded as features. Thus, for each period the number of the features thus obtained was a multiple of the number of the electrodes and the number of the frequency bands. In the present Example, the number of the electrodes was sixty and the number of the frequency bands were three. Thus, 60×3 (180) features (normalized powers of the ECoG data) were obtained for each period.

Moreover, in association with the data clipping, an observer inputted, from the input section 10 to the electric prosthetic arm control device 20, which class of body movement the patient performed.

As a result of performing the body movement task one time, the decoder training set creating section 11 created training set data including the data indicating which class of body movement the patient performed, and the data indicative of the m number of the features obtained during the period (0 to +1 second period) when the patient performed the body movement. The training set data was stored in a recording section (not illustrated) of the decoder training set creating section 11. The body movement task was repeated plural times for each class of the body movements in the same manner, whereby the decoder training set data creating section 11 created plural sets of training set per body movement. The plural sets of training set data for each class of the body movements were recorded in a recording section (not illustrated) of the decoder training set creating section 11.

[2.1.3. Generation of Decoders]

After the plural sets of training set data for each class of the body movements were recorded in a recording section (not illustrated) of the decoder training set creating section 11, the first decoder generating section 12 performed supervised learning based on all the training set data stored in the recording section of the decoder training set creating section 11 at the time. The supervised learning generated first decoders 5 which were classifiers. In the present Example, the classifiers (first estimation model) were support vector machines. That is, in the present Example, the first decoder generating section 12 generated decoders respectively for all the sets of the training set data. The decoders were for classification using linear support vector machine (SVM), where inputs were the m numbers of features of the ECoG data, and outputs were the classes of the body movements that the patient performed. The linear support vector machine plotted each first training set data as data points in n dimensional space whose coordinates were the m number of features of the ECoG data. The linear support vector machine could classify the data points into data point groups (classes) according to the outputs (the classes of the body movement that the patient performed). Further, the linear support vector machine could find out a separation plane (hyperplane) which was most distanced from a data point nearest thereto. By determining on which side of the classification plane data points corresponding to brain information data (the m number of the features), the linear support vector machine performed the classification of the brain information data.

For the multi-class classifications using the support vector machine, a program called "brain decoder toolbox" (which is to be disclosed soon) was used, which was developed by Advanced Telecommunications Research Institute International (ATR), Computational Neuroscience Laboratories, Department of Neuroinformatics. This program is also employed in the following literature: Kamitani, Y. and F. Tong, Decoding the visual and subjective contents of the human brain. Nature Neuroscience, 8(5): 679-85, 2005.

[2.1.4. Evaluation on Generalization Capability]

In the same manner described above, the patient again carried out the movement task in response to the audio stimulus presented by the stimulus presenting device 50, and powers for the frequency bands was extracted per electrode as the features by the feature extracting section 3 from ECoG data clipped by the data clipping section 2 for the 0 second to +1 second period with respect to the audio stimulus. Then, by using the first decoders 5 generated at S2, the class of the body movement performed by the patient was estimated from the features of the ECoG data.

This process is repeated plural times for each body movement. Every time the patient performed the body movement of the movement task in response to the audio stimulus, the first decoders 5 performed the estimation on the class of the body movement performed by the patient, from the features of the ECoG data. In the present Example, the patient repeated the movement task about 20 to 40 times for each body movement.

Based on the data thus obtained, a correct rate (generalization capability) of the estimation performed by the first decoders 5 was calculated by the correct rate estimating section 13 and the normalized mutual information calculating section 14 using k-fold cross validation. In the present Example, the correct rate estimating section 13 and the normalized mutual information calculating section 14 performed 5-fold cross validation for all the data obtained as the result of the movement task carried out the by the patient, so as to evaluate the first decoders 5 in terms of their generalization capability.

In particular, the present Example was carried out as follows. The decoder training set creating section 11 created the decoders in which the data indicative of the class of the body movement performed by the patient were paired respectively with the data indicative of the m number of features of the ECoG data occurred at the time (during 0 second to +1 second) when the patient performed the body movement. For each of the body movement, about 20 to 40 pairs of such data were created. Then, the decoder training set creating section 11 shuffled the all the data sets once. First ⅘ of the all data pairs was sent to the first decoder generating section 12 so that the ⅘ of the all data pairs would be used as the training data. The first decoder generating section 12 generated the first decoders 5 by the learning (learning using the support vector machine) in which the first ⅘ of the all data pairs was used as the training data. Further, the decoder training set creating section 11 sent the rest (⅕) of all data pairs to the correct rate estimating section 13 and the normalized mutual information calculating section 14 so that the rest (⅕) of all data pairs would be used as test data. The test was performed such that the correct rate estimating section 13 and the normalized mutual information calculating section 14 sent the m number of features of the test data to the first decoders 5, and the first decoders 5 estimated, from the m number of features of the test data, which class of the body movement the patient performed. The first decoders 5 returned the result of the estimation to the correct rate estimating section 13 and the normalized mutual information calculating section 14. The correct rate estimating section 13 and the normalized mutual information calculating section 14 calculated the correct rate that indicated a probability at which the estimation correctly estimated the class of the body movement that the patient actually performed (the body movement of the patient according to the test data), i.e., a probability at which the class of the body movement estimated and the class of the body movement actually performed by the patient were equal. In the present Example, the correct rate calculated by the correct rate estimating section 13 and the normalized mutual information calculating section 14 was normalized mutual information between the m number of features and the result (class of the body movement) of the estimation, the normalized mutual information being normalized so that an average of the mutual information for the three periods became zero. The learning and test was repeated 5 times with different ⅘ and ⅕ of the data pairs, so as to calculate the correct rate 5 times. The generalization capability of the first decoders 5 was an average of the five readings of the correct rate.

The mutual information is a measure of mutual dependence between two random variables. Typically, the mutual information is in units of bits. Mutual information between two discrete random variables X and Y is defined as follows:

$$I(X;Y) = \sum_{y \in Y} \sum_{x \in X} p(x,y) \log \frac{p(x,y)}{p(x)p(y)}$$

where p(x, y) is simultaneous distribution function of X and Y, p(x) and p(y) are marginal probability density function of X and Y, respectively. The mutual information is a measure of information amount shared by X and Y, and indicates how accurately one of the variables can be estimated from the other of the variables. For example, in case X and Y are totally independent from each other, to know information on X can not be any help of obtaining information of Y, and vice versa. In this case, the mutual information is zero. On the other hand, if X and Y are identical with each other, X and Y share all the information therebetween. Thus, to know the information of X means to know the information of Y, and vice versa.

As described above, the first machine learning phase, as illustrated in FIG. 3, the patient performed a particular class of body movement in response to the audio stimulus, and the brain signals (ECoG) of the patient were measured at the time when the patient performed the body movement. From the combinations (first training data) of the brain signal (ECoG) data and the body movements performed by the patient, the first decoders 5 were prepared by the classification using the algorism of the linear support vector machine. Then, the ECoG data was newly obtained for the body movement again performed by the patient, and the estimation on the class of the body movement was carried out by using the first decoders 5. The estimation was evaluated to find the generalization capability (mutual information) of the first decoders 5. One example of the mutual information thus calculated is showed in the center column (0 second to 1 second) in FIG. 8(a).

[2.2. Second Machine Learning Phase]

The second decoder generating section 15 created second training set data in which the data indicative of the m number of features in the 5 sets of the test data used in the 5-fold cross validation were paired respectively with the data indicating the normalized mutual information calculated from the m number of features by the correct rate estimating section 13 and the normalized mutual information calculating section 14. Then, the second decoder generating section 15 performed supervised learning using all the pairs of the second training set data, so as to create an correct rate estimation model (second estimation model) for estimating the mutual information (correct rate) from the features of the ECoG data. The correct rate estimation model was used as the second decoders 6. In the present Example, the correct rate estimation model) was to perform the estimation based on Gaussian process regression (GPR) using the linear covariance functions.

The Gaussian process regression predicts an output value from linear regression model Y=f(x), f(x)=X'W, where X is a measure value (feature) from which the estimation is made, and Y* is the output value (normalized mutual information) to be estimated by the estimation. Assume that W and Y* are Gaussian process, the predicted distribution p(f*) based on the linear regression model can be obtained by calculating expectation E [f(X) f(X')] which is a product of their function values for any pair of X and X' of an input vector.

The Gaussian process regression is explained in further details in, for instance: C. E. Rasmussen and C. K. I. Williams, "Gaussian Processes for Machine Learning", The MIT Press, 2006; and C. M. Bishop, "Pattern Recognition and Machine Learning", Springer, 2006.

The Gaussian process regression is one kind of Bayesian approach and performs model-based estimation from training data and pretest probability of a model by weighted integral of posterior probability of a parameter of the model. It is said the use of the Gaussian process regression allows estimation without much over fitting or under fitting, even in case the amount of the training data is small.

For example, the Gaussian process regression can be performed by using a tool box for Gaussian process regression, disclosed in a home page on the Internet (URL: http://www-.gaussianprocess.org/gpml/code/gpml-matlab.zip).

The inputs for the Gaussian process regression (inputs for the second decoder generating section 15) were the normalized mutual information prepared by the correct rate estimating section 13 and the normalized mutual information calculating section 14 by normalizing the mutual information of the ECoG data in each of the three periods (−1 second to 0 second, 0 second to 1 second, and 1 second to 2 second) according to the average of the mutual information of the three periods.

[2.3. Free Movement]

[2.3.1. Estimation of Movement Timing]

In the same manner as described above, the patient performed a body movement freely, and an m number of features (powers per frequency band and per electrode) were extracted from the free body movement of the patient. Every 200 millisecond (predetermined time period), the normalized mutual information (correct rate) was estimated by the second decoders 6. In the present Example, by using the estimation model based on the Gaussian process regression the second decoders 6 estimated mutual information for 1-second period from the m number of the ECoG data of 1-second periods (between 1 second before the present time and the present time) (for 5 cycles). One example of the mutual information estimated from the training data is shown in the central column (0 to 1 second) in FIG. 8(b).

Then, the judging section 7 judged whether the normalized mutual information (correct rate) thus estimated was over a certain threshold or not. Only a period in which the normalized mutual information (correct rate) thus estimated was over the certain threshold was estimated as being suitable for the estimation of the class of the body movement (this period corresponds to the period in which the patient performed the body movement). Thus, only during such a period, the estimation on the class of the body movement performed by the patient was performed from the m number of the features of the ECoG data by the first decoders 5.

[2.3.2. Robot Control Method]

Next, according to S10 to S13 in FIG. 2 described above, the electric prosthetic arm control section 8 controlled in real time the electric prosthetic arm 60 based on the class of the patient's body movement estimated by the first decoders 5 at S10.

In the present Example, the electric prosthetic arm 60 was one developed by Professor Hiroshi YOKOI at the University of Electro-Communications, who is one of the inventors of the present invention. The electric prosthetic arm was configured to be driven by a servomotor controlled by a microcomputer. At the time the present Example was performed, only fingers and elbow of the electric prosthetic arm could be controlled, even though it is planned to elaborate the electric prosthetic arm to be movable in shoulder as well. In the present Example, a control command (control signal) including 13 sets of control parameter values was transmitted from the electric prosthetic arm control section 8 to the microcomputer of the electric prosthetic arm 60 via a serial port (not illustrated) of the electric prosthetic arm control device 20, whereby the electric prosthetic arm control section 8 controlled the electric prosthetic arm 60 to perform an upper limb movement as estimated by the above-described classification.

For the free movement in which, as described above, the patient performed any of the body movements at arbitrary timings without the audio stimulus, the ECoG (brain signals) of the patient was measured as illustrated in FIG. 4, and timing and class of the body movement was estimated from the ECoG data (brain signals) by the first decoders 5 prepared by the learning based on the correspondence between the features and the body movements recorded in the machine learning phase. The electric prosthetic arm 60 (robot) was manipulated according to the estimation. It was proved that the machine system of the present Example can allow an almost-untrained person to control the electric prosthetic arm 60 freely in the three-dimensional space. Thus, it was found that the machine system of the present Example can cause the electric prosthetic arm 60 to emulate the estimated body movement in real time.

[Evaluation on Movement Timing Estimation Accuracy]

Next, movement timing estimation accuracy in the method according to the present Example was evaluated.

As a Comparative Example for the Evaluation, a method of estimating a movement timing from features of ECoG data by the support vector machine, the features of ECoG data being obtained from free movement performed by the patient.

Results of the estimation are shown in FIGS. 6(a) and 6(b). The estimation shown in FIGS. 6(a) and 6(b) were carried out with different estimation sensitivities. In FIGS. 6(a) and 6(b), EMG_Onset indicates, by height along the vertical axis, movement start timings determined by electromyogram (EMG) measured, and the classes of body movements performed at the timing. SVM_Onset indicates signals of the result of the estimation on the movement timings according to the method of Comparative Example (this signal shows power of 1 at the movement timing, and power of 0 if the moment is not the movement timing). Moreover, FIG. 7 shows a distribution of time periods from the estimated movement start timings (peaks of SVM_Onset) to movement start timings closest thereto (the time periods corresponds to estimation errors), which are respectively shown in FIGS. 6(a) and 6(b).

From FIGS. 6(a), 6(b), and 7, it can be understood that the comparative method frequently makes such a misestimation that it is a movement timing in absence of a patient body movement. Thus, the method of the Comparative Example has a large estimation error in the estimation of the movement timing.

Next, the method according to the method of the Example of the present invention for estimating the movement timing from the features of the ECoG data obtained from the patient's free movement was carried out (the method of estimating the movement timing according to the Example was such that a period in which the correct rate estimated from the features of the ECoG data by the Gaussian process regression was above a threshold is estimated as a movement timing).

Figure 9:
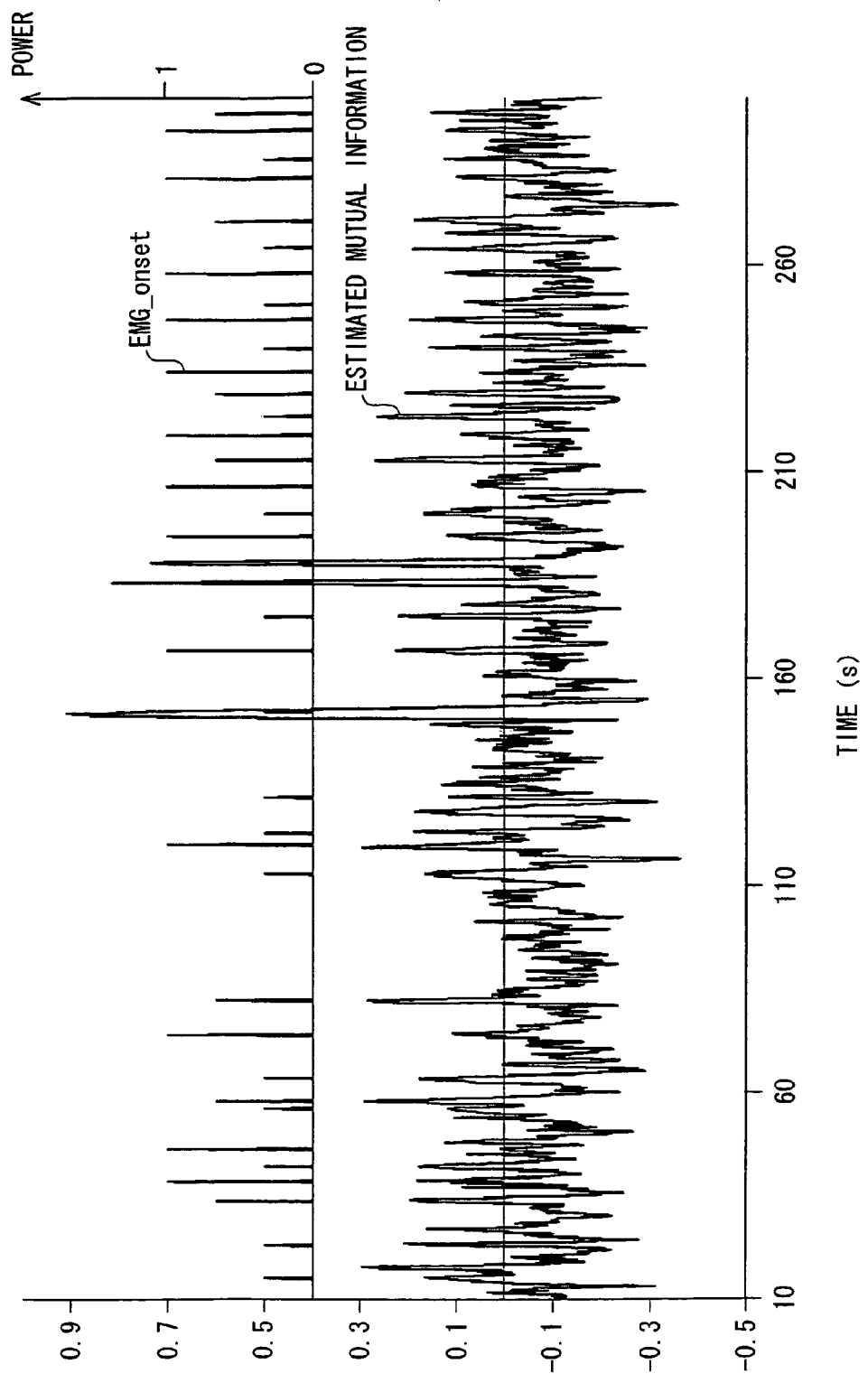
FIG. 9 is a graph illustrating a relationship between the estimated mutual information in Example of the present invention and actual movement timings.
Figure 10:
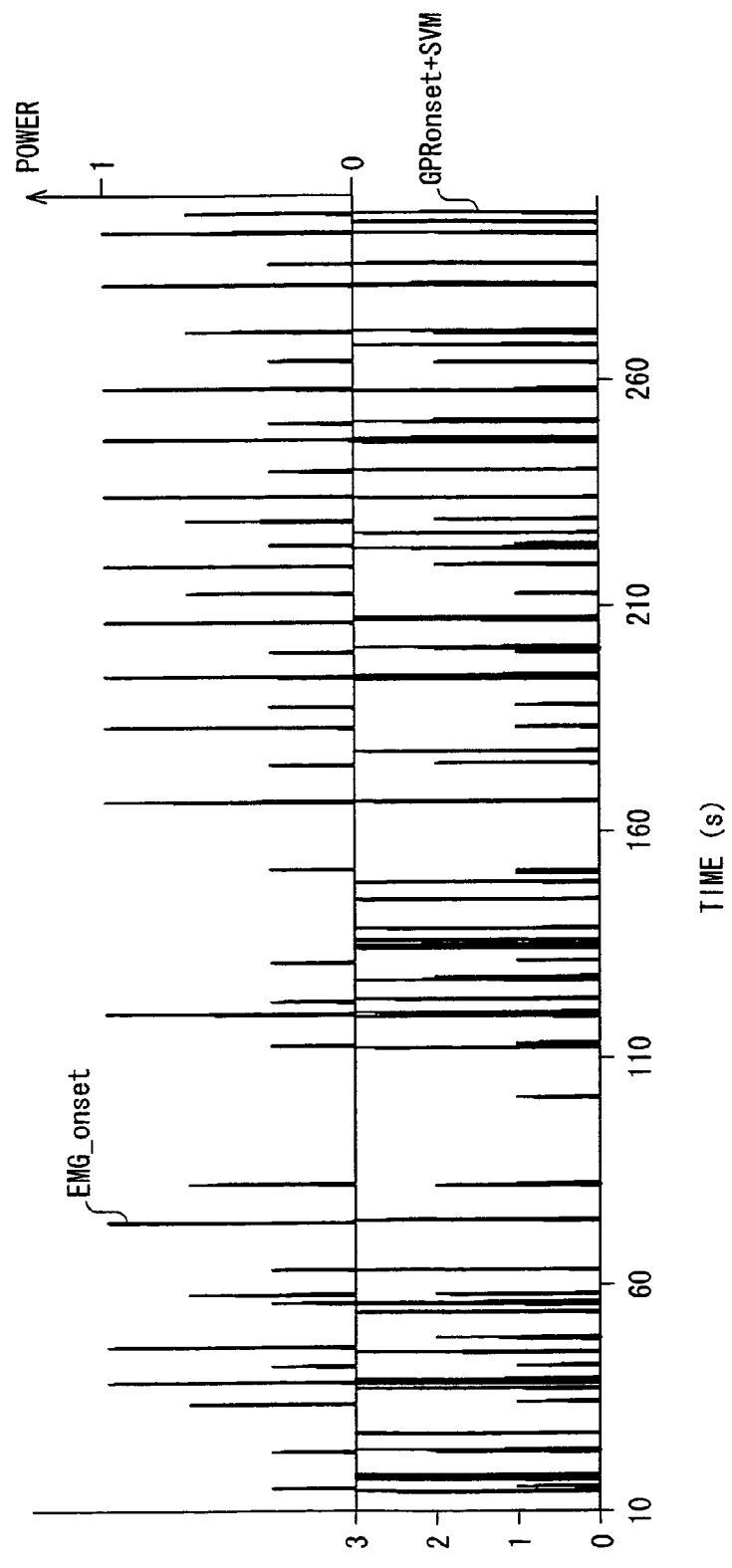
FIG. 10 is a graph illustrating a result of estimation on movement timings according to an estimation method according to Example of the present invention.
Figure 11:
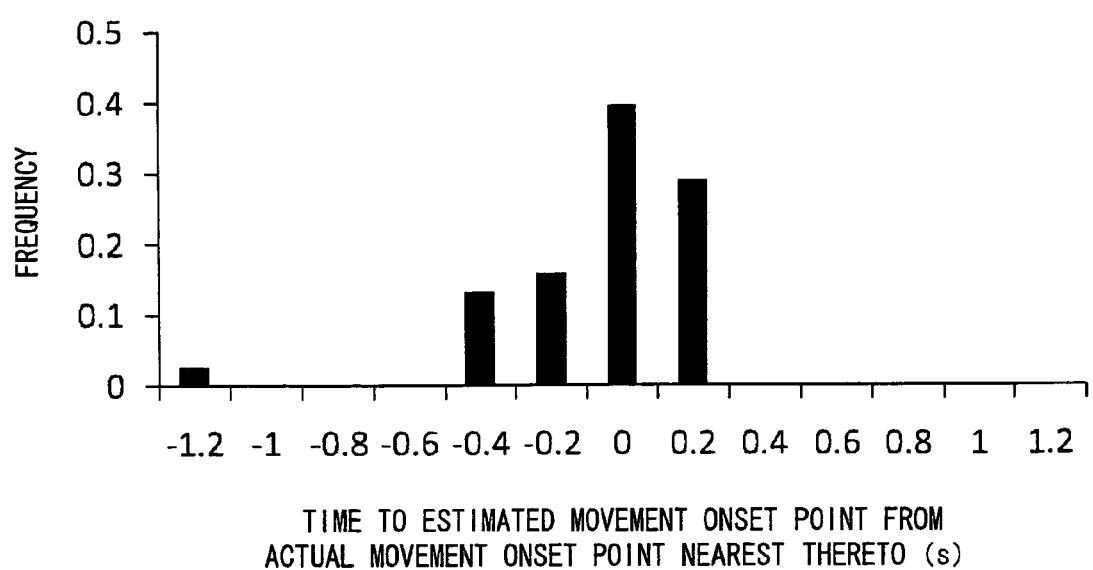
FIG. 11 is a graph illustrating errors in the estimation on movement timings according to the estimation method according to Example of the present invention.

Results of the estimation is shown in FIG. 10. The correct rate (movement estimation accuracy) estimated by the method according to the Example is illustrated in FIG. 9. In FIGS. 9 and 10, EMG_Onset indicates, by the height along the vertical axis, movement start timings determined by EMG and the classes of the body movements performed at the timings. In FIG. 10, GPRonset+SVM indicates the movement timings estimated according to the Example, and the classes of the body movements (indicated by values of 1 to 3) estimated by the first decoders at the timings (at the movement timings, any one of the values of 1 to 3 to indicate the classes of the body movements is shown, and 0 is shown if the moment is not the movement timing). Moreover, FIG. 11 shows a distribution of time periods from the estimated movement start timings (peaks of GPRonset+SVM) to movement start timings closest thereto (the time periods corresponds to estimation errors), which are respectively shown in FIG. 10.

From FIG. 9, the peaks of the estimated correct rate substantially match with the movement start timings. Moreover, the comparisons between FIGS. 6(a), 6(b), and 10, and between FIGS. 7 and 11 show that the method according to the Example less frequently misestimated as a movement timing a timing which is in absence of an actual body movement, and that the method according to the Example can estimate the movement timing with less errors. Thus, the method according to the Example makes it possible to perform the estimation of the movement timing more accurately.

[Reference Example: Evaluation on Data Clipping Period]

In the Example, the ECoG data in the 0 second to +1 second period with respect to the timing of the detection of the TTL signal corresponding to the sound "Po" was clipped from the ECoG data obtained when the patient performed a body movement. The period to be clipped was determined based on the result of the experiment below.

In the same manner as described in "2.1.2. Collection of First Training Data", ECoG data obtained when the patient performed a body movement was supplied to the data clipping section 11. Next, the ECoG data in the −1 second to +2 second period with respect to the timing of detecting the TTL signal corresponding to the sound "Po" (i.e. the period between 1 second before the detection of the TTL signal and 2 second after the detection of the TTL signal) was clipped by the data clipping section 11. The clipped ECoG data was divided into these for the three periods namely, the −1 second to 0 second period, the 0 second to +1 second period, and +1 second to +2 second period. Next, from the clipped ECoG data in these periods, the feature extracting section 3 calculated powers per electrode for the three frequency bands which were also chosen for the data collection for the resting state. Further, the feature extracting section 12 normalized the powers of the ECoG data per electrode for the three frequency bands for these periods with respect to the power obtained in the resting state, thereby obtaining 60×3 features (normalized powers) each period.

Then, in the same manner as in the Example, the decoder training set creating section 2 created about 20 to 40 sets of training data for each of combinations of the three periods and the plural classes of body movements, and then recorded the training data in the recording section for the decoder training set creating section 11. After that, in the same manner as in the Example, the decoder generating section 4 generated, from the training set data, three classes of decoders 0-1 to 0-3 for the respective three periods. The decoders 0-1 to 0-3 were for the estimation of the classes of the body movements performed by the patient.

Figure 8:
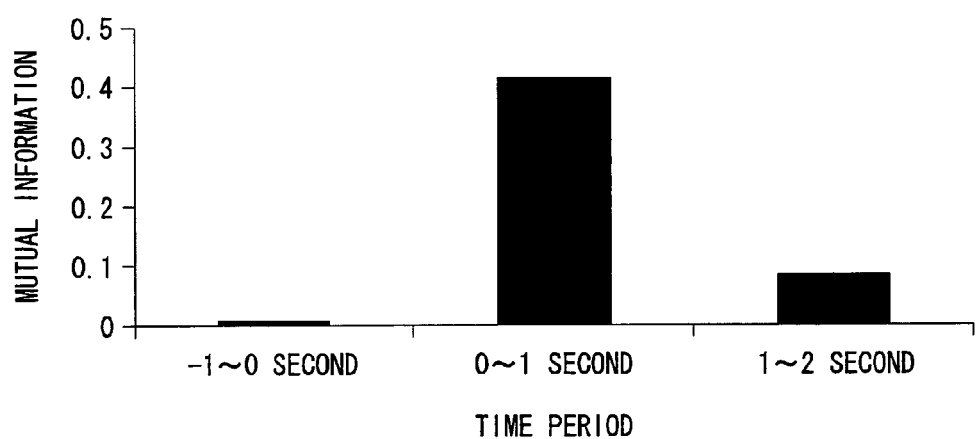
FIGS. 8(a) and 8(b) are graphs illustrating calculated mutual information and estimated mutual information in Example of the present invention and Referential Example.
Figure 8:
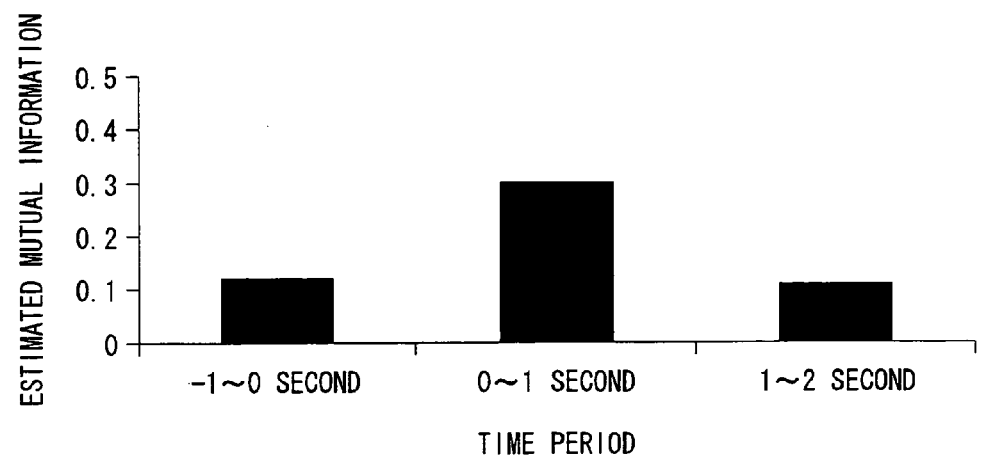

From the ECoG data of the three periods (−1 second to 0 second period, 0 second to +1 second period, and +1 second to +2 second with respect to the time when the patient performed the body movement), the classes of the body movement performed by the patient were estimated by using the three classes of decoders 0-1 to 0-3, respectively. Then, mutual information (movement estimation accuracy; correct rate) between the ECoG data and results (classes of body movements) of the estimations performed with the decoders 0-1 to 0-3 was calculated for each of the three periods. FIG. 8(*a*) shows the mutual information thus obtained. This result shows that these periods provide different amounts of information on the ECoG to the estimation of the body movements, and the movement estimation accuracy (mutual information) of the decoders generated from the ECoG data in the 0 second to +1 second was higher than the others.

Moreover, in the same manner as the Example, one mutual information estimation model (correct rate estimation model) was created for estimating mutual information in the three periods (−1 second to 0 second period, 0 second to +1 second period, and +1 second to +2 second period with respect to the time when the patient performed a body movement) from the ECoG data of the periods based on the second training data in which the ECoG data obtained in the three periods was paired respectively with the results (classes of body movement) of the estimation performed by the decoders 0-1 to 0-3 from the ECoG data. The mutual information estimation model used the Gaussian process regression as in the Example. Based on the mutual information estimation model, the mutual information in the respective three periods was estimated from the ECoG data in the three periods. FIG. 8(*b*) shows the mutual information thus obtained. This result demonstrates that the mutual information estimated by the mutual information estimation model using the Gaussian process regression showed the same quantitative transition as the mutual information used in the learning. That is, it was proved that the use of this model can quantitatively estimate, merely from ECoG data, how the mutual information obtained from the movement estimation based on the ECoG data will transit.

These results showed the decoders 0-2 learned with all the data in the 0 second to +1 second had a generalization capability higher than the others, and therefore, the Example used the decoders 0-2 as the first decoders 5. Moreover, the mutual information estimation model (second decoder) in the Example was the model created from the ECoG data in the aforementioned three periods.

INDUSTRIAL APPLICABILITY

The present invention is applicable to various BMI techniques. BMI techniques are expected to be mainly applied for heavily physically impaired people for now and near future. For example, the BMI techniques are applied for patients suffering from amyotrophic lateral sclerosis (ALS) (the number of new patients per annum: about 700 persons, Prevalence: about 7,000 persons), Amputation (the number of new patients per annum: about 5,000 persons, Prevalence: about 147,000 persons), Palsy due to spiral cord injury (the number of new patients per annum: about 5,000 persons, Prevalence: about 100,000 persons), post-stroke locked-in syndrome, etc. The present invention can enable such a patient to control a robotic arm or the like machine as he/she desires, thereby making it possible to provide him/her with a better quality of life, and to reduce burden on caring or nursing the patient. Further, the present invention is expected to allow such a patient to resume productive activity thereby regaining an income source that the patient has lost once. Besides, the BMI techniques are expected to be applied to healthy persons in the future. The present invention provides an important fundamental technique for BMI.

It is expected that, by using a machine control device according to the present invention in combination with an implanted ECoG measuring device for measuring ECoG and wirelessly sending brain signals of ECoG, locked-in syndrome patients suffering from locked-in syndrome spinal cord injury, amyotrophic lateral sclerosis, or the like can control a machine as he/she desires, in the course of day-to-day activities.

Moreover, the machine control device of the present invention may be applied in such a way that a control signal is sent to a computer so that positional movement of a cursor (pointer) on the computer is controlled by the brain signals. In this case, for example, the cursor may be controlled to move rightward when a user images closing his right hand (or straightening his right elbow), move leftward when the user images opening his right hand (or flexing his right elbow), to move downward when a user images closing his left hand (or straightening his left elbow), and to move upward when the user imaging opening his left hand (or flexing his left elbow). The present invention allows patients heavy impaired in motor functions to control various other machines, such as remote controllers for electric devices (television, lights, air conditioner, etc.), electrical wheel chairs, electrical bed, etc., by brain signals as they desire.

It is preferable that the machine control device according to the present invention further comprises a brain signal measuring device for measuring electrocorticogram as the brain signals. This makes it possible to obtain the brain signal information more stably, thereby allowing more stable control of the machine.

It is preferable that the machine control device according to the present invention further comprises a brain information extracting section for extracting powers of the brain signals in plural frequency bands from the brain signals, the powers of the brain signals being the information of the brain signals. This makes it possible to obtain the brain signal information in a larger amount, thereby allowing more accurate body movement estimation and machine control.

The machine control device according to the present invention is especially effective when the machine to control is a robot for emulating at least part of the human body, and the first to nth postures are postures of the robot corresponding to the first to nth body postures. In this case, the machine control device according to the present invention can allow the robot to perform a natural and human-like movement.

In the machine control device according to the present invention, the estimation section preferably uses a classifier as the first estimation model. Examples of the classifier encompass support vector machine, neural network, Gaussian process regression modified for classification, sparse logistic regression modified for classification, etc. With this, more accurate body movement estimation and machine control can be attained with a shorter computation time.

In the machine control device according to the present invention, the correct rate estimating section preferably uses a regression model as the second estimation model. Examples of the regression model encompass Gaussian process regression, linear discriminant analysis (LDA), sparse logistic regression (SLR), etc. This makes it possible to perform accurate estimation with training data collected a small number of times.

In the machine control device according to the present invention, it is preferable that the correct rate is mutual information between the information of the brain signals of the user and a result of the estimation performed from the information by using the first estimation model, the mutual information being calculated by k-fold cross validation. This makes it possible to avoid such erroneous operation that the posture of the machine is changed when the user does not perform nor image a body movement.

If the correct rate estimating section uses a Gaussian process regression as the second estimation model, the correct rate is preferably calculated by normalizing the mutual information between the user's brain signal information thus obtained by the k-fold cross validation and the result of the estimation performed based on the first estimation model from the brain signal information, the mutual information being normalized such that an average of the mutual information obtained by plural times validation is zero. This makes it possible to estimate the correct rate more accurately.

REFERENCE SIGNS LIST

3: Feature Extracting Section (brain information extracting section)
5: First Decoders (estimating section)
6: Second Decoders (correct rate estimating section)
7: Judging Section
8: Electric Prosthetic Arm Control Section (machine control section)
20: Electric Prosthetic Arm Control Device (main part of machine control device)
30: Subdural Electrodes (part of machine control device;)
60: Electric Prosthetic Arm (machine)

The invention claimed is:

1. A machine control device for controlling a machine based on brain signals of a user, comprising:

an estimating unit for, by using a first estimation model developed in advance by supervised learning with a plurality of first training sets, estimating, from information of brain signals of the user, which one of a plurality of body movements the user performs or images, each of said plurality of first training sets being constituted by a pair consisting of (i) a body movement performed or imaged by the user and (ii) information of brain signals of the user corresponding to said body movement performed or imaged by the user, each of said plurality of body movements going toward a first to an nth body posture where n is an integer not less than 2;

a correct rate estimating unit for estimating a correct rate from said information of brain signals by using a second estimation model developed in advance by supervised learning with a plurality of second training sets, each of said plurality of second training sets being constituted by a pair consisting of (iii) a previously estimated correct rate and (iv) information of brain signals of the user corresponding to said previously estimated correct rate, each correct rate indicating a probability that a body movement estimated by said estimation unit and a body movement performed or imaged by the user match;

a judging unit for judging whether or not a correct rate estimated by said correct rate estimating unit exceeds a predetermined threshold value; and a machine control unit for controlling the machine according to a result estimated by said estimating unit, so as to change a posture of the machine between ones of said first to nth postures through at least one intermediate posture therebetween, such that said change between one of said first to nth postures to another of said first to nth postures includes a plurality of substeps of change, the first to the nth postures being respectively associated with the first to nth body postures, wherein:

said estimating unit provides an estimation of body movement that the user performs or images to the machine control unit only if said judging unit judges that a correct rate estimated by said correct rate estimating unit exceeds said predetermined threshold value, and if the posture of the machine is not currently identical with the posture associated with the body posture toward which a body movement estimated by said estimating unit goes, the machine control unit changes the posture of the machine by performing a part of said substeps of change toward the posture associated with the body posture toward which the body movement estimated by the estimating unit goes.

2. The machine control device as set forth in claim 1, further comprising:

a brain signal measuring device for measuring electrocardiogram as the brain signals.

3. The machine control device as set forth in claim 2, further comprising:

a brain information extracting unit for extracting powers of the brain signals in plural frequency bands from the brain signals, the powers of the brain signals being the information of the brain signals.

4. The machine control device as set forth in claim 1, wherein:

the machine is a robot that emulates at least part of a human body, and the first to nth postures are postures of the robot corresponding to the first to nth body postures.

5. The machine control device as set forth in claim 1, wherein:

the estimating unit uses a classifier as the first estimation model.

6. The machine control device as set forth in claim 1, wherein:

the correct rate estimating unit uses a regression model as the second estimation model.

7. The machine control device as set forth in claim 1, wherein:

the correct rate is mutual information between the information of the brain signals of the user and a result of the estimation performed from the information by using the first estimation model, the mutual information being calculated by k-fold cross validation.

8. A machine system comprising:
a machine control device as set forth in claim 1; and
a machine controlled by the machine control device.

9. A non-transitory computer-readable storage medium wherein a machine control program for causing a computer to function as the units of a machine control device as set forth in claim 1 is stored.

10. A method for controlling a machine based on brain signals of a user, comprising:

using an estimating unit, performing a first learning step of, by using first supervised learning with a plurality of first training sets, creating a first estimation model for use in estimating, from information of brain signals of the user, which one of a plurality of body movements the user performs or images, each of said plurality of first training sets being constituted by a pair consisting of (i) a body movement performed or imaged by the user and (ii) information of brain signals of the user corresponding to said body movement performed or imaged by the user, each of said plurality of body movements going toward a first to an nth body posture where n is an integer not less than 2;

using a correct rate estimation unit, performing a correct rate calculating step of calculating a correct rate indicating a probability that a body movement estimated by the first estimation model in accordance with input of information of brain signals of the user and a body movement performed or imaged by the user match; and performing a second learning step of, by using second supervised learning with a plurality of second training sets, creating a second estimation model for use in estimating a correct rate, each of the second training sets being constituted by a pair consisting of (iii) a previously estimated correct rate and (iv) information of brain signals of the user corresponding to said previously estimated correct rate;

using a judging unit, performing a judging step of judging whether or not a correct rate estimated by the second estimation model in accordance with input information of brain signals of the user exceeds a threshold value;

performing an estimating step of, if it is judged in the judging step that the correct rate exceeds the threshold value, using the first estimation model to estimate from the information of the brain signals of the user, which one of said plurality of body movements the user performs or images and providing the estimation to a machine control unit; and performing a machine control step of using the machine control unit to control the machine according to a body movement estimated in the estimating step, so as to change a posture of the machine between ones of said first to nth postures through at least one intermediate posture therebetween, such that said change between one of said first to nth postures to another of the first to nth postures includes a plurality of substeps of change, the first to the nth postures being respectively associated with the first to nth body postures, wherein:

if an estimation is performed in the estimating step and if the posture of the machine is not currently identical with the posture associated with the body posture toward which the body movement estimated in the estimating step goes, the posture of the machine is changed in the machine control step by performing a part of the substeps of change toward the posture associated with the body posture toward which the body movement estimated in the estimating step goes.

\* \* \* \* \*